US012564332B2

(12) United States Patent　　　　　　(10) Patent No.:　US 12,564,332 B2
O'Brien et al.　　　　　　　　　　　　　(45) Date of Patent:　　　Mar. 3, 2026

(54) WEARABLE DEVICE FOR MEASURING A PERSON'S VENTILATION OR METABOLISM METRICS

(71) Applicant: VO2 Master Health Sensors Inc., Vernon (CA)

(72) Inventors: Peter O'Brien, Vernon (CA); Zachary Birkett, Vernon (CA); Stephen Ito-Dyck, Vernon (CA); James Webber, Vernon (CA); Aidan Demers, Vernon (CA)

(73) Assignee: VO2 MASTER HEALTH SENSORS INC., Vernon (CA)

( * ) Notice: Subject to any disclaimer, the term of this patent is extended or adjusted under 35 U.S.C. 154(b) by 784 days.

(21) Appl. No.: 17/876,052

(22) Filed: Jul. 28, 2022

(65) Prior Publication Data

US 2024/0032818 A1　　Feb. 1, 2024

(51) Int. Cl.
*A61B 5/083*　　　　(2006.01)
*A61B 5/00*　　　　(2006.01)
(Continued)

(52) U.S. Cl.
CPC .......... *A61B 5/0836* (2013.01); *A61B 5/0833* (2013.01); *A61B 5/097* (2013.01);
(Continued)

(58) Field of Classification Search
CPC ..... A61B 5/0836; A61B 5/0833; A61B 5/097; A61B 5/6803; A61B 5/0816;
(Continued)

(56) References Cited

U.S. PATENT DOCUMENTS 3,661,528 A　　5/1972　Falk
3,735,752 A　　5/1973　Rodder
(Continued)

FOREIGN PATENT DOCUMENTS

CA　　2430613　　11/2004
EP　　0794806　　2/1996
(Continued)

OTHER PUBLICATIONS

Supplementary European Search Report dated Sep. 25, 2024 issued on European Patent Application No. EP 21878818.
(Continued)

*Primary Examiner* — Andrey Shostak
(74) *Attorney, Agent, or Firm* — Nicholas Garner; Oyen Wiggs Green & Mutala LLP

(57)　　　　ABSTRACT

There is provided a device for measuring a person's ventilation or metabolism metrics. The device includes a conduit shaped to receive an exhalation of air therethrough. The device includes at least one gas sensor passively sampling said exhalation of air by means of a positive or negative pressure differential. The device includes a pump configured to assist in said passive sampling. The pump is configured to adjust the flow rate of a sample portion of said exhalation of air passing through to the at least one gas sensor, so as to be proportional or linear within a predetermined threshold, to the flow rate of the exhalation of air passing through the conduit.

The device is configured to operate via both breath-mixing and breath-by-breath modes using a single flow path. The device is configured to change between the breath-mixing and breath-by-breath modes as a function of operation of the pump.

20 Claims, 10 Drawing Sheets

(51) Int. Cl.
    *A61B 5/097*     (2006.01)
    *G01N 1/24*     (2006.01)
    *G01N 33/497*     (2006.01)

(52) U.S. Cl.
    CPC ............. *A61B 5/6803* (2013.01); *G01N 1/24*
    (2013.01); *G01N 33/497* (2013.01)

(58) Field of Classification Search
    CPC .... A61B 2560/0242; A61B 2562/0247; A61B
    5/087; G01N 1/24; G01N 33/497
    See application file for complete search history.

(56) References Cited

U.S. PATENT DOCUMENTS

| | | | |
|---|---|---|---|
| 3,924,467 A | 12/1975 | Takamura et al. | |
| 4,142,407 A | 3/1979 | Kuroiwa et al. | |
| 4,197,857 A | 4/1980 | Osborn | |
| 4,292,978 A | 10/1981 | Guth | |
| 4,297,871 A | 11/1981 | Wright et al. | |
| 4,404,859 A | 9/1983 | Ohsawa et al. | |
| 4,440,177 A | 4/1984 | Anderson et al. | |
| 4,620,248 A | 10/1986 | Gitzendanner | |
| 4,658,832 A | 4/1987 | Brugnoli | |
| 4,705,543 A | 11/1987 | Kertzman | |
| 4,736,750 A | 4/1988 | Valdespino et al. | |
| 4,808,201 A | 2/1989 | Kertzman | |
| 5,072,737 A | 12/1991 | Goulding | |
| 5,184,501 A * | 2/1993 | Lewis ................. | G01N 1/2252 |
| | | | 73/23.31 |
| 5,363,857 A | 11/1994 | Howard | |
| 5,705,735 A | 1/1998 | Acorn | |
| 5,857,461 A | 1/1999 | Levitsky et al. | |
| 5,913,249 A | 6/1999 | Weckstrom | |
| 5,957,127 A | 9/1999 | Yamamori et al. | |
| 6,206,837 B1 | 3/2001 | Brugnoli | |
| 6,435,183 B1 | 8/2002 | Farman | |
| 6,572,561 B2 | 6/2003 | Mault | |
| 6,612,306 B1 | 9/2003 | Mault | |
| 6,629,933 B1 | 10/2003 | Lindner | |
| 6,629,934 B2 | 10/2003 | Mault et al. | |
| 6,815,211 B1 | 11/2004 | Blazewicz et al. | |
| 6,899,683 B2 | 5/2005 | Mault et al. | |
| 6,955,650 B2 | 10/2005 | Mault et al. | |
| 6,983,663 B2 | 1/2006 | Fathollahzadeh | |
| 7,108,659 B2 | 9/2006 | Ross et al. | |
| 7,618,235 B2 | 11/2009 | Sacco | |
| 7,621,271 B2 | 11/2009 | Brugnoli | |
| RE41,332 E | 5/2010 | Binder | |
| 7,730,793 B2 | 6/2010 | Speldrich | |
| 8,002,712 B2 | 8/2011 | Meka et al. | |
| 8,197,417 B2 | 6/2012 | Howard et al. | |
| 8,684,900 B2 | 4/2014 | Tran | |
| 9,498,150 B2 | 11/2016 | Colman et al. | |
| 9,706,965 B2 | 7/2017 | Colman et al. | |
| 10,271,766 B1 | 4/2019 | Parker, Jr. et al. | |
| 10,381,849 B2 | 8/2019 | Wing et al. | |
| 11,284,814 B2 | 3/2022 | O'Brien et al. | |
| 2002/0100474 A1 | 8/2002 | Kellner et al. | |
| 2003/0028120 A1 | 2/2003 | Mault et al. | |
| 2003/0065274 A1 | 4/2003 | Mault et al. | |
| 2003/0208132 A1 | 11/2003 | Baddour | |
| 2003/0208133 A1 | 11/2003 | Mault | |
| 2004/0094155 A1 | 5/2004 | Castor et al. | |
| 2004/0186390 A1 | 9/2004 | Ross et al. | |
| 2005/0004488 A1 | 1/2005 | Hoppe et al. | |
| 2005/0154386 A1 | 7/2005 | West et al. | |
| 2007/0093725 A1 | 4/2007 | Shaw | |
| 2007/0107728 A1 | 5/2007 | Ricciardelli et al. | |
| 2010/0036272 A1 | 2/2010 | Mace et al. | |
| 2011/0319783 A1 | 12/2011 | Lindholt et al. | |
| 2012/0234696 A1 | 9/2012 | Mosley et al. | |
| 2013/0267803 A1 | 10/2013 | Kramer | |
| 2013/0331726 A1 | 12/2013 | Weber | |
| 2014/0024960 A1 | 1/2014 | Smith et al. | |
| 2014/0276171 A1 | 9/2014 | Hestness et al. | |
| 2014/0364758 A1 | 12/2014 | Schindhelm et al. | |
| 2014/0378792 A1 | 12/2014 | Krimsky et al. | |
| 2015/0083121 A1 | 3/2015 | Fisher et al. | |
| 2017/0049978 A1 | 2/2017 | Berg et al. | |
| 2017/0055875 A1 * | 3/2017 | Candell ................ | A61B 5/4866 |
| 2017/0119279 A1 | 5/2017 | Ahmad | |
| 2017/0135605 A1 | 5/2017 | Sandholt et al. | |
| 2017/0173262 A1 | 6/2017 | Veltz | |
| 2018/0153440 A1 | 6/2018 | Lee et al. | |
| 2019/0110714 A1 | 4/2019 | O'Brien et al. | |
| 2019/0120821 A1 * | 4/2019 | Atsalakis ............... | A61B 5/087 |
| 2020/0022618 A1 | 1/2020 | Mcclung et al. | |
| 2020/0121222 A1 | 4/2020 | Becker et al. | |
| 2021/0076979 A1 * | 3/2021 | O'Brien ................ | A61B 5/097 |
| 2021/0378546 A1 | 12/2021 | Xian et al. | |
| 2022/0031987 A1 | 2/2022 | Wysoski | |
| 2022/0211295 A1 | 7/2022 | O'Brien et al. | |

FOREIGN PATENT DOCUMENTS

| | | |
|---|---|---|
| EP | 0911051 | 4/1999 |
| EP | 2606820 A1 | 6/2013 |
| EP | 2670491 A2 | 12/2013 |
| EP | 2769673 A1 | 8/2014 |
| EP | 2259723 | 5/2016 |
| EP | 3028627 B1 | 7/2016 |
| WO | 9118279 | 11/1991 |
| WO | 0028881 | 5/2000 |
| WO | 2001008554 | 2/2001 |
| WO | 03010496 | 2/2003 |
| WO | 2004041084 A1 | 5/2004 |
| WO | 2008060165 | 5/2008 |
| WO | 2008064062 | 5/2008 |
| WO | 2015127994 A1 | 9/2015 |
| WO | 2016138380 A1 | 9/2016 |
| WO | 2017177340 | 10/2017 |
| WO | 2019173894 | 9/2019 |
| WO | 2020076855 A1 | 4/2020 |
| WO | 2022077101 A1 | 4/2022 |

OTHER PUBLICATIONS

"Venturi", Merriam-Webster Online and found on the WayBackMachine archived page dated Feb. 19, 2010: https://web.archive.org/web/20100219215417/https://www.merriam-webster.com/dictionary/venturi.

"Venturi effect", as set out in the archived version of the Wikipedia page for the same dated Jan. 6, 2015: https://en.wikipedia.org/w/index.php?title=Venturi_effect&oldid=641227804.

International Search Report for PCT/CA2017/050467, dated Aug. 17, 2017.

Written Opinion for PCT/CA2017/050467, dated Aug. 17, 2017.

"Series LX-Valve" product specification, from Parker Hannifin Corp., dated Mar. 2016.

International Search Report and Written Opinion for PCT/CA2018/051314, dated Jan. 8, 2019.

European Search Report dated Jan. 17, 2020 for EP 17 78 1693.

J. C. T. Pepperell et al. "P139 The use of venturi masks with oxygen concentrators", Thorax, vol. 66, No. Suppl. 4, Dec. 1, 2011, pp. A123-A124, XP055649271, GB, ISSN: 0040-6376, DOI:10.1136/thoraxjnl-2011-201054c.139.

"Technology Overview: COSMED Wearable Metabolic Systems", COSMED, The Metabolic Company, dated Sep. 25, 2020. https://web.archive.org/web/20200925164533/https://www.cosmed.com/hires/WP_COSMED_wearable_metabolic_technology_EN.pdf.

International Search Report and Written Opinion for PCT/CA2021/051431, dated Jan. 12, 2022.

European Search Report dated Nov. 12, 2021 for EP18909533.4.

European Search Report for European Patent Application No. 23186942.1, completed Oct. 27, 2023 (mailed Nov. 7, 2023).

\* cited by examiner

WEARABLE DEVICE FOR MEASURING A PERSON'S VENTILATION OR METABOLISM METRICS

BACKGROUND OF THE INVENTION

Field of the Invention

There is provided a wearable device. In particular, there is provided a wearable device for measuring ventilation or metabolism metrics in the form of a fully self-contained metabolic analyzer worn on the face/head, used for the measurement of volume of consumed oxygen (VO2), volume of expired carbon dioxide (VCO2), minute ventilation (VE), and many other metrics derived therefrom (e.g. Rf, Tv, FeO2 etc).

Description of the Related Art

U.S. patent Ser. No. 11/284,814 to O'Brien et al. discloses a device for measuring a user's oxygen-consumption. The device includes a venturi tube. The venturi tube has a first tapered portion, a second tapered portion that is more tapered compared to the first tapered portion, and a constriction between the portions thereof. The device includes at least one pressure sensor in communication with the constriction and the first tapered portion of the venturi tube. The device includes an oxygen sensor in communication with the constriction and the first tapered portion of the venturi tube. United States Patent Application Publication No. 2021/0076979 A1 to O'Brien et al. discloses a device for measuring a person's ventilation. The device includes a conduit with an exhaled-air receiving portion and an inhaled-air receiving portion. The device includes pressure and oxygen sensor sampling ports. The sampling ports are in fluid communication with the conduit. The device includes a deflector disposed within the conduit. The deflector is configured to deflect air exhaled into the exhaled-air receiving portion of the conduit away from the sensor ports.

Each of the above devices is a completely face/head worn metabolic analyzer used in the measurement of oxygen consumption (VO2), ventilation, and several metrics therefrom (e.g. Rf, Tv, FeO2). The devices use passive flow through sample lines thereof with the use of a venturi to bring gas to the oxygen sensor. The user's breath passes through a venturi whereby the difference in velocity of fluid between a proximal cross-section and throat of the venturi creates a pressure difference that passively flows a proportion of gas through a sample line without substantially resisting the user's breathing. This passive flow design uses a tiny portion of the energy generated from the user's breathing, thereby enabling the device to be compact, wearable and portable on the one hand.

The proportion of the flow entering the sample line corresponds to the inherent linearity of the venturi, which may be imperfect in real world applications on the other hand, compared to conventional testing systems that may be more precise but which are larger, relatively bulky and stationary in nature. There may be two major constraints in employing passive side-stream sampling: proportionality to the mainstream may be inconsistent and subject to the user's breathing frequency and tidal volume; and low ventilations from the user's breathing generate insufficient pressure differentials to purge the gas sample line and accompanying dead space. Also, adding a carbon dioxide (CO2) sensor to one of the above devices as-is may increase side-stream dead space so much such that the sample line is never purged sufficiently, thus invalidating any gas sensor measurements.

There accordingly may be a need for an improved device which is wearable, portable and energy efficient like those devices referred to above on the one hand, while being more versatile and compact on the other hand, with the flow through the sample line being yet more proportional to that through the venturi or primary conduit through which exhalations pass, such that if both gas streams were captured and perfectly mechanically mixed their gas concentrations (% O2, % CO2, % N2 etc) would be equal within a predetermined threshold.

BRIEF SUMMARY OF INVENTION

There is provided, and it is an object to provide, an improved device for measuring a person's ventilation or metabolism metrics disclosed herein, as well as a method for the same.

There is accordingly provided a device for measuring a person's ventilation or metabolism metrics according to one aspect. The device includes a conduit shaped to receive an exhalation of air therethrough. The device includes at least one gas sensor in fluid communication with the conduit and configured to passively sample the exhalation of air by means of a positive or negative pressure differential. The device includes a pump configured to adjust the flow rate of the sample of said exhalation of air passing through the sample line so as to be proportional within a predetermined threshold, to the flow rate of the exhalation of air passing through the conduit.

There is also provided a device for measuring a person's ventilation or metabolism metrics according to another aspect. The device includes a conduit shaped to receive an exhalation of air therethrough. The device includes at least one gas sensor in communication with the conduit via a sample line. The device includes a restriction within the conduit and configured to promote flow of a portion of the exhalation of air through said sample line to the at least one gas sensor. The device includes a pump configured to adjust the flow rate through the sample line to the at least one gas sensor to promote a flow rate through the sample line that is proportional within a predetermined threshold, to the exhalation of air passing through the conduit.

There is further provided a device for measuring a person's ventilation or metabolism metrics according to a further aspect. The device includes a conduit shaped to receive an exhalation of air therethrough. The device includes at least one gas sensor passively sampling said exhalation of air by means of a positive or negative pressure differential. The device includes a pump configured to assist in said passive sampling.

There is additionally provided a device for measuring a person's ventilation or metabolism metrics according yet another aspect. The device includes a conduit through which an exhalation of air passes. The conduit is shaped to create a pressure differential therewithin. The device includes a gas sampling chamber. The device includes a gas sensor in communication with the gas sampling chamber and the conduit via a sample line. The gas sensor is supplied the exhalation of air by means of positive or negative said pressure differential. The device includes a pump configured to increase the flow rate through the sample line to the at least one gas sensor such that the volume of exhaled air passing into the gas sampling chamber per said exhalation of air is less than the volume of the gas sampling chamber for each said exhalation of air.

There is yet also provided a device for measuring a person's ventilation or metabolism metrics according to yet a further aspect. The device includes a conduit through which an exhalation of air passes. The conduit is shaped to create a pressure differential therewithin. The device includes a gas sampling chamber. The device includes a gas sensor in communication with the gas sampling chamber and the conduit via a sample line. The gas sensor is supplied the exhalation of air by means of positive or negative said pressure differential. The device includes a pump configured to increase the flow rate through the sample line to the at least one gas sensor such that the volume of exhaled air passing into the gas sampling chamber per said exhalation of air is generally or substantially equal to the volume of the gas sampling chamber for each said exhalation of air.

There is yet additionally provided a device for measuring a person's ventilation or metabolism metrics according to another aspect. The device includes a conduit through which an exhalation of air passes. The conduit is shaped to create a pressure differential therewithin. The device includes a gas sampling chamber. The device includes a gas sensor in communication with the gas sampling chamber and the conduit via a sample line. The gas sensor is supplied the exhalation of air by means of positive or negative said pressure differential. The device includes a pump configured to increase the flow rate through the sample line to the at least one gas sensor such that the volume of exhaled air passing into the gas sampling chamber per said exhalation of air is greater than the volume of the gas sampling chamber for each said exhalation of air.

There is also provided a device for measuring a person's ventilation or metabolism metrics according to a further aspect. The device includes a conduit with a pressure differential being formed with exhaled air passing therethrough. The device includes at least one gas sensor in fluid communication with the conduit via a sample line. The device uses passive flow to direct exhaled air to the at least one gas sensor. The device includes a pump which dynamically adjusts the flow of said exhaled air through the sample line to the at least one gas sensor such that a sample line said flow rate is proportional within a predetermined threshold, to a primary said flow rate passing through the conduit.

There is further provided a method of measuring a person's ventilation or metabolism metrics according to one aspect. The method includes providing a conduit via which a primary portion of an exhalation of air passes. The method includes passively sampling a secondary portion of the exhalation of air by means of a positive or negative pressure differential and directing said sample to at least one gas sensor. The method includes adjusting the flow rate of the secondary portion of the exhalation of air to be proportional within a predetermined threshold, to the flow rate of the primary portion of the exhalation of air passing through the conduit.

There is also provided a method of measuring a person's ventilation or metabolism metrics according to another aspect. The method includes providing a conduit shaped to receive an exhalation of air therethrough. The method includes passively sampling the exhalation of air by means of a positive or negative pressure differential. The method includes assisting the passive sampling of the exhalation of air via a pump.

There is further provided a device for measuring a person's ventilation or metabolism metrics according to yet another aspect. The device includes a conduit shaped to receive an exhalation of air therethrough. The device includes at least one gas sensor in fluid communication with the conduit and configured to passively sample the exhalation of air by means of a positive or negative pressure differential. The device is configured to operate via both breath-mixing and breath-by-breath modes using a single flow path.

There is additionally provided a device for measuring a person's ventilation or metabolism metrics according to yet a further aspect. The device includes a conduit shaped to receive one or more exhalations of air therethrough. The device includes at least one gas sensor. The device includes a gas sampling chamber in fluid communication with the gas sampling chamber. The at least one gas sensor is configured to passively sample the one or more exhalations of air by means of a positive or negative pressure differential. The device includes a pump via which the device is configured to selectively change from a breath-mixing mode to a breath-by-breath mode by selectively adjusting the extent to which the pump increases the flow rate of the portion of said one or more exhalations of air being sampled.

There is also provided a device for measuring a person's ventilation or metabolism metrics according to another aspect. The device includes a conduit shaped to receive one or more exhalations of air therethrough. The device includes at least one gas sensor within a gas sampling chamber in fluid communication with the conduit. The at least one gas sensor is configured to passively sample the one or more exhalations of air by means of a positive or negative pressure differential together with pump assistance.

It is emphasized that the invention relates to all combinations of the above features, even if these are recited in different claims.

Further aspects and example embodiments are illustrated in the accompanying drawings and/or described in the following description.

BRIEF DESCRIPTION OF DRAWINGS

The accompanying drawings illustrate non-limiting example embodiments of the invention.

DESCRIPTION OF THE PREFERRED EMBODIMENTS

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

Figure 1:
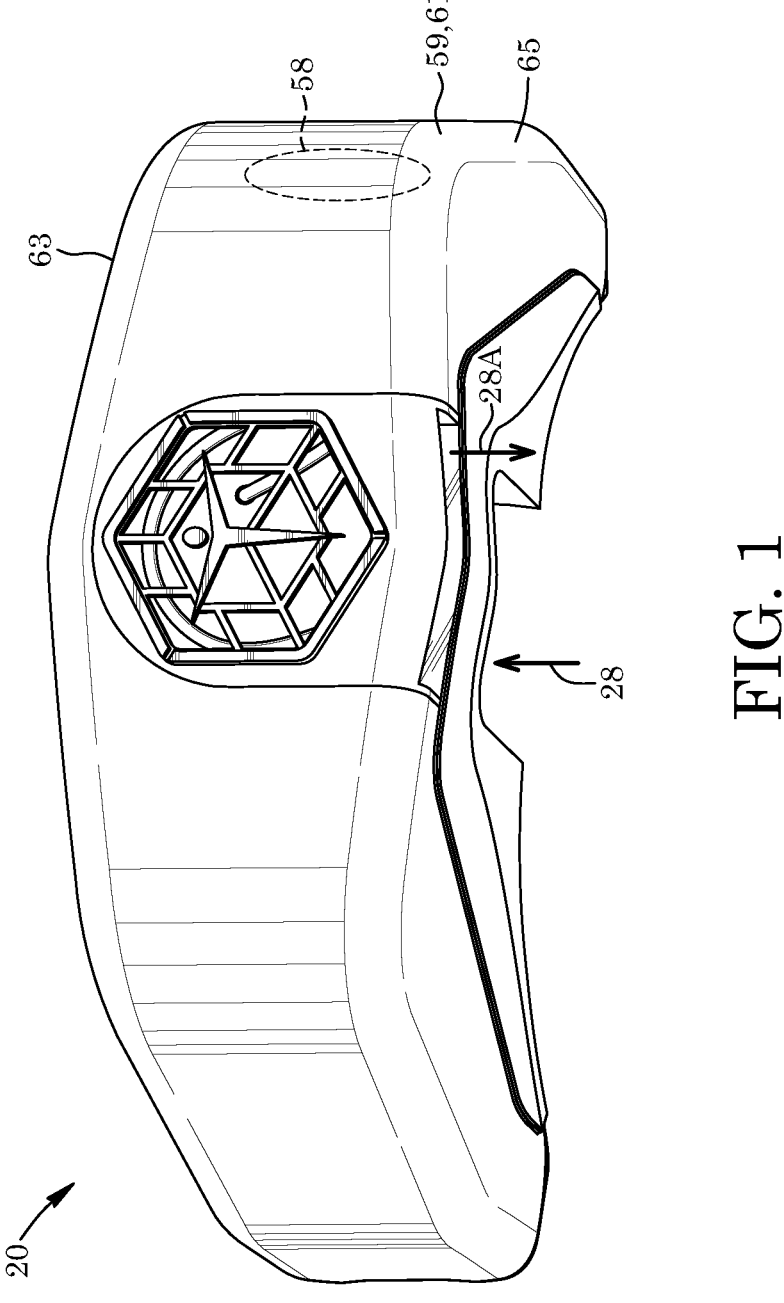
FIG. 1 is a front, right side perspective view of a device for measuring a person's ventilation and/or metabolism metrics according to one aspect.
Figure 6:
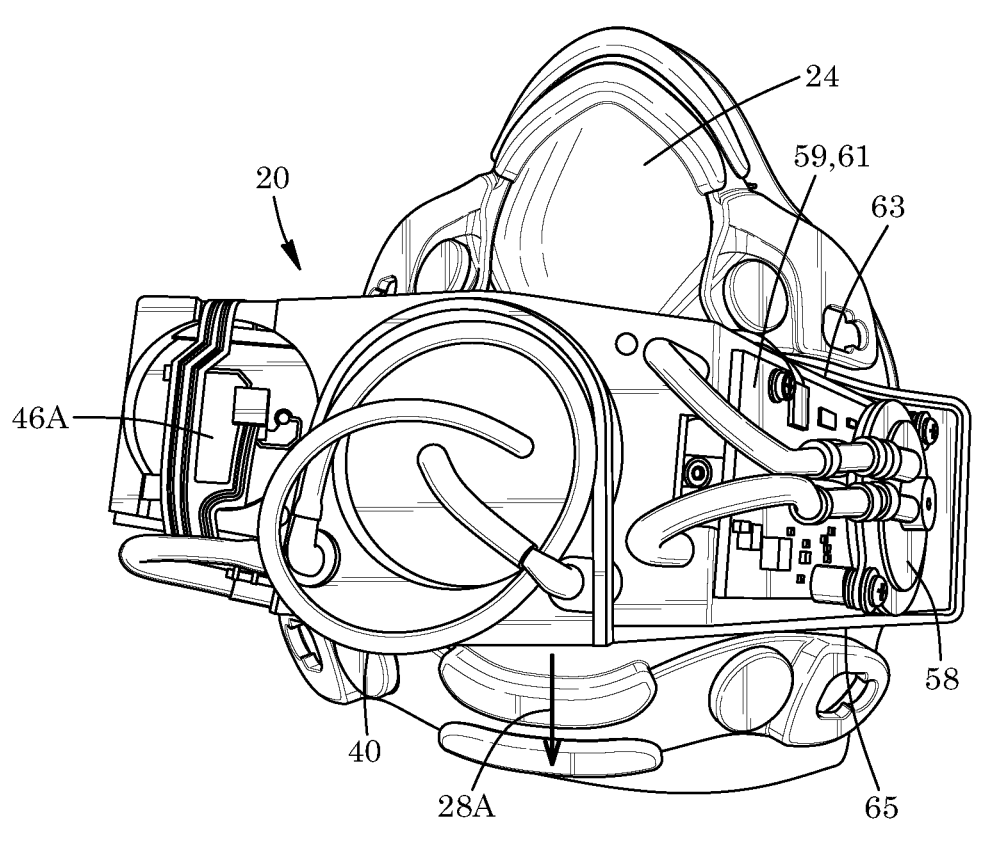
FIG. 6 is a front, left side perspective view of the device of FIG. 4 together with a facemask to which the device is coupled, with a dehumidification cartridge assembly thereof shown removed to reveal interior parts thereof.

Referring to the drawings and first to FIG. 1, there is shown a device 20 for measuring a person's ventilation and/or metabolism metrics. FIG. 1 shows a non-limiting example of the device and devices of other shapes and sizes may be used in other embodiments. Device 20 may be referred to as a device for measuring a person's ventilation or oxygen-consumption, or may be referred to as a metabolic or ventilation analyzer, for example. The device is shaped and sized to be face-mounted and/or head-worn. Device 20 includes a connector 22, seen in FIG. 4, which is shaped to selectively couple to a facemask 24 shown in FIG. 6. The device is configured to be portable and wearable, and may be referred to as a wearable device.

Figure 2:
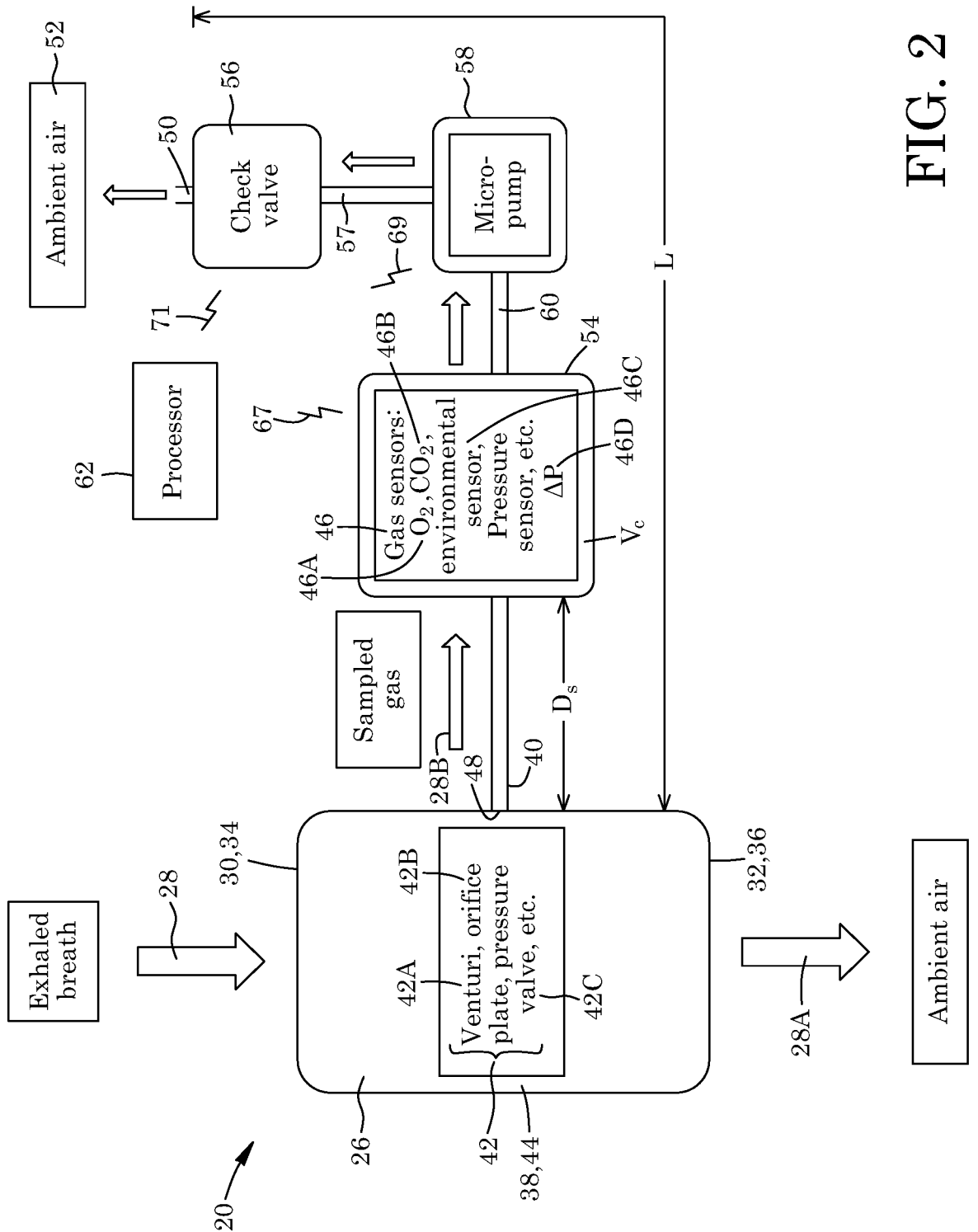
FIG. 2 is a schematic diagram of the device of FIG. 1, showing the flow path of an exhalation of air passing through a conduit thereof, with a portion of the exhalation of air passing through a sample line to one or more gas sensors within a gas sampling chamber, with the portion of the exhalation of air being obtained via passive sampling with supplementary pump assistance.
Figure 4:
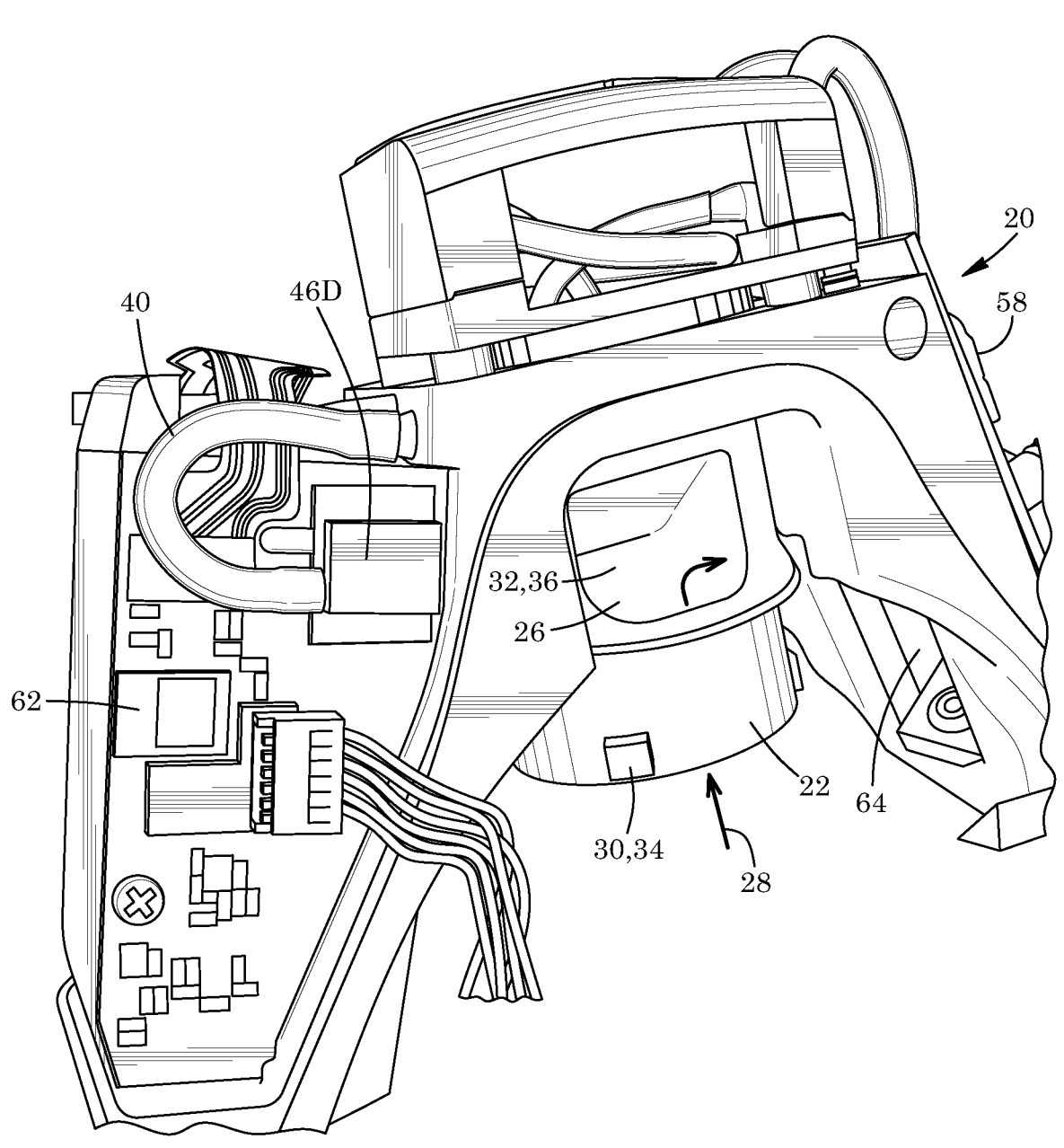
FIG. 4 is a bottom perspective view of the device of FIG. 2, with an outer shell thereof being removed.

As seen in FIG. 4, device 20 includes a first or primary conduit 26 shaped to receive an exhalation of air 28 therethrough between proximal and distal openings 30 and 32 of the conduit. As seen in FIG. 2, the conduit is shaped to receive a primary portion 28A of exhalation of air 28 therethrough. Conduit 26 has a first end portion 34 adjacent proximal opening 30 and a second end portion 36 spaced-apart from the first end portion thereof. The second end portion of the conduit is adjacent distal opening 32 in this example. Conduit 26 includes an intermediate portion 38 between end portions 34 and 36 thereof.

Still referring to FIG. 2, device 20 includes a first or secondary conduit or sample line 40 in fluid communication with conduit 26. The sample line may be referred to as a sampling line. Sample line 40 is positioned between first end portion 34 and second end portion 36 of conduit 26. The sample line is shaped to receive a secondary or sample portion 28B of exhalation of air 28 therethrough. The length L of sample line 40 is relatively short, with a length equal to or less ten inches in one example, equal to or less than eight inches in another example, and between seven to eight inches in a further example. However, these length ranges are not strictly required and sample line 40 may have a different length in other embodiments.

Device 20 includes a means for passive sampling 42 with a restriction 44 in exhalation of air 28 promoting flow of sample portion 28B of the exhalation of air through an alternative path or sample line 40. In this example conduit 26 is configured to create a pressure differential therewithin via the restriction. The conduit is configured to form a pressure differential therewithin when exhalation of air 28 passes therethrough. Conduit 26 may comprise a venturi or venturi tube 42A, with restriction 44 comprising a constriction thereof; however, this is not strictly required and the restriction may take other forms in other embodiments. Examples of conduits and devices which describe use of a venturi tube to create a pressure differential therewithin when exhalations of air pass therethrough are found in U.S. patent Ser. No. 11/284,814 and United States Patent Application Publication No. 2021/0076979 A1 to O'Brien et al., the disclosures of which are incorporated herein by reference.

Means for passive sampling 42 and/or restriction 44 may comprise intermediate portion 38 of conduit 26, where the intermediate portion of the conduit has a cross-sectional area less than at least one of first and second end portions 34 and 36 of the conduit. As a further alternative, the means for passive sampling and/or restriction may comprise an orifice plate 42B with a side stream said sample line 40 in fluid communication therewith. As yet a further alternative, the means for passive sample and/or restriction may comprise a pressure valve 42C. These means for passive sampling are intended to be non-limiting and device 20 may include other means, mechanisms or configurations for creating a pressure differential which facilitates such sampling in other embodiments.

As seen in FIG. 2, the device includes at least one and in this example a plurality of gas sensors 46. The gas sensors are in fluid communication with conduit 26 via sample line 40. Device 20 is configured to inhibit the distance of separation $D_S$ between conduit 26 and gas sensors 46. The gas sensors in this example are adjacent to the conduit.

Means for passive sampling 42 and/or restriction 44 are configured to promote flow of sample portion 28B of exhalation of air 28 through the sample line to gas sensors 46. The gas sensors are supplied the sample portion of the exhalation of air by means of positive or negative pressure differential resulting from the restriction. Gas sensors 46 are thus configured to passively sample the exhalation of air by means of the positive or negative pressure differential.

The gas sensors include an oxygen sensor, in this case a galvanic oxygen sensor 46A. Gas sensors 46 include in this example a carbon dioxide ($CO_2$) sensor, in this example a nondispersive infrared (NDIR) $CO_2$ sensor 46B. The gas sensors in this example include an environmental sensor 46C. Gas sensors 46 include a flow sensor, in this example a pressure sensor, in this case a differential said pressure sensor 46D. The pressure sensor is used to determine breath state or flow rate. Flow is measured via differential pressure sensor 46D with a first port 48 at restriction 44 in the flow path 28 and a second port 50 measuring ambient pressure or air 52. The differential pressure sensor is used to determine the flow rate of sample portion 28B of exhalation of air 28 passing through sample line 40. The above are non-limiting examples of gas sensors 46 and other types of gas sensors may in addition or alternatively be used in other embodiments.

Device 20 includes a gas sampling chamber 54 in fluid communication with gas sensors 46. The gas sampling chamber may be referred to as a gas mixing chamber in some instances or a gas sensing chamber. Gas sampling chamber 54 may be shaped to enclose gas sensors 46 at least in part. Gas sensors 46 and the gas sampling chamber couple to and are in fluid communication with conduit 26 via sample line 40 in this example.

Device 20 includes a one-way valve, in this example a check valve 56. The check valve is in fluid communication with and in this example downstream of gas sensors 46. Check valve 56 is configured to inhibit backflow through sample line 40.

Device 20 includes a pump 58. Check valve 56 is downstream of the pump in this example and in fluid communication with the pump via a passageway, in this example hose 57. However, this is not strictly required and the check valve may be situated anywhere along sample line 40. Pump 58 in addition or alternatively may include check valve 56 therewithin and/or as a part thereof.

Figure 5:
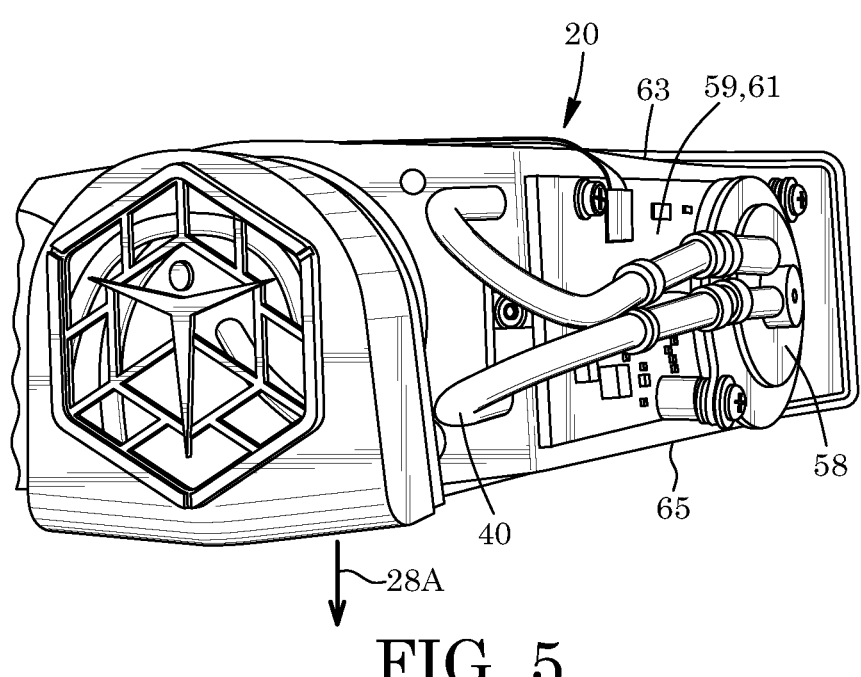
FIG. 5 is a front, left side perspective view thereof.

Referring to FIG. 5, the pump is a microfluidic pump or micropump in this example. Pump 58 in this example is an off-the-shelf product, in this case a TTP-Ventus™ pump that may be purchased at TTP-Ventus Limited, having an address at Melbourn Science Park, Melbourn Hertfordshire, SG8 6EE, United Kingdom. However, this is not strictly required and other types of pumps may be used in other embodiments. Pump 58 in one non-limiting example weighs five grams or less; however, here too this is not strictly required the pump may weigh more than or less than this in other embodiments. The pump in this example outputs a minimal sound level of less <10 dB and has a control precision of <0.1%; however, this likewise is not strictly required. Pump 58 uses resonance frequencies to maximize its output flow for minimal power input in this example.

As seen in FIG. 5, the pump has a relatively small form factor of approximately equal to or less than 3 centimeters by 2 centimeters in one example and a form factor of approximately equal to or less than 3 centimeters by 1 centimeter in another example; however, this is not strictly required and the pump may have a form factor that is larger and/or different in other embodiments. In one non-limiting example, pump 58 has a form factor of 29 millimeters by 11 millimeters. The pump is shaped to extend along the side 59 or a side portion 61 of device 20. Pump 58 in this example is shaped to extend between top 63 and bottom 65 of the device. The pump in this example is shaped to be positioned adjacent the user's face and mask 24 seen in FIG. 6; however, this is not strictly required.

As seen in FIG. 2, pump 58 is in fluid communication with gas sensors 46 and couples to gas sampling chamber 54 via a passageway, in this example hose 60. The pump is downstream of the gas sensors in this example; however, this is not strictly required.

Device 20 includes a processor 62. The processor is in communication with gas sensors 46, pump 58 and check valve 56 as shown schematically by arrows with numerals 67, 69 and 71. Device 20 includes a power source, in this example a battery 64 to power gas sensors 46D, processor 62 and pump 58. The battery is portable and may comprise a AA-type battery, AAA-type battery or similar such battery; however, the latter is not strictly required and other types of portable batteries may be used in other embodiments.

Processor 62 is configured to receive various inputs from gas sensors 46 and determine therefrom the volume of consumed oxygen (VO2) in the exhalation of air 28 and the volume of expired carbon dioxide (VCO2) in the exhalation of air. The volume of consumed oxygen (VO2) and the volume of expired carbon dioxide (VCO2) are determined based on ventilation and the gas concentration of the exhalation of air which are time aligned in this example. Processor 62 is configured to receive various inputs from gas sensors 46 and quantify therefrom one or more aspects of a person's ventilation, including but not limited to: minute ventilation; respiratory frequency (Rf); respiratory quotient (Rq); tidal volume (Tv); fraction of expired oxygen (FeO2); fraction of inspired oxygen (FiO2); fraction of expired carbon dioxide (FeCO2); and fraction of inspired carbon dioxide (FiCO2).

The processor is configured to receive flow rate data for conduit 26 and sample line 40. The processor is configured to i) determine the extent to which the flow rate of sample portion 28B of exhalation of air 28 passing through the sample line must be increased to achieve proportionality between flow rates 28A and 28B within a predetermined threshold and ii) actuate pump 58 based on the same. Referring to FIG. 2, the pump is thus configured to adjust the flow rate of sample portion 28B of exhalation of air 28 passing through sample line 40 so as to be proportional within a predetermined threshold, to flow rate 28A of the exhalation of air passing through conduit 26. In this example the pump via processor 62 dynamically adjusts flow of the sample portion of the exhalation of air passing through the sample line to gas sensors 46 such that the sample line flow rate of air is proportional within a predetermined threshold, to the primary flow rate of air passing 28A through the conduit. Pump 58 of device 20 is thus configured to assist in the passive sampling 28B of exhalation of air 28.

Figure 7:
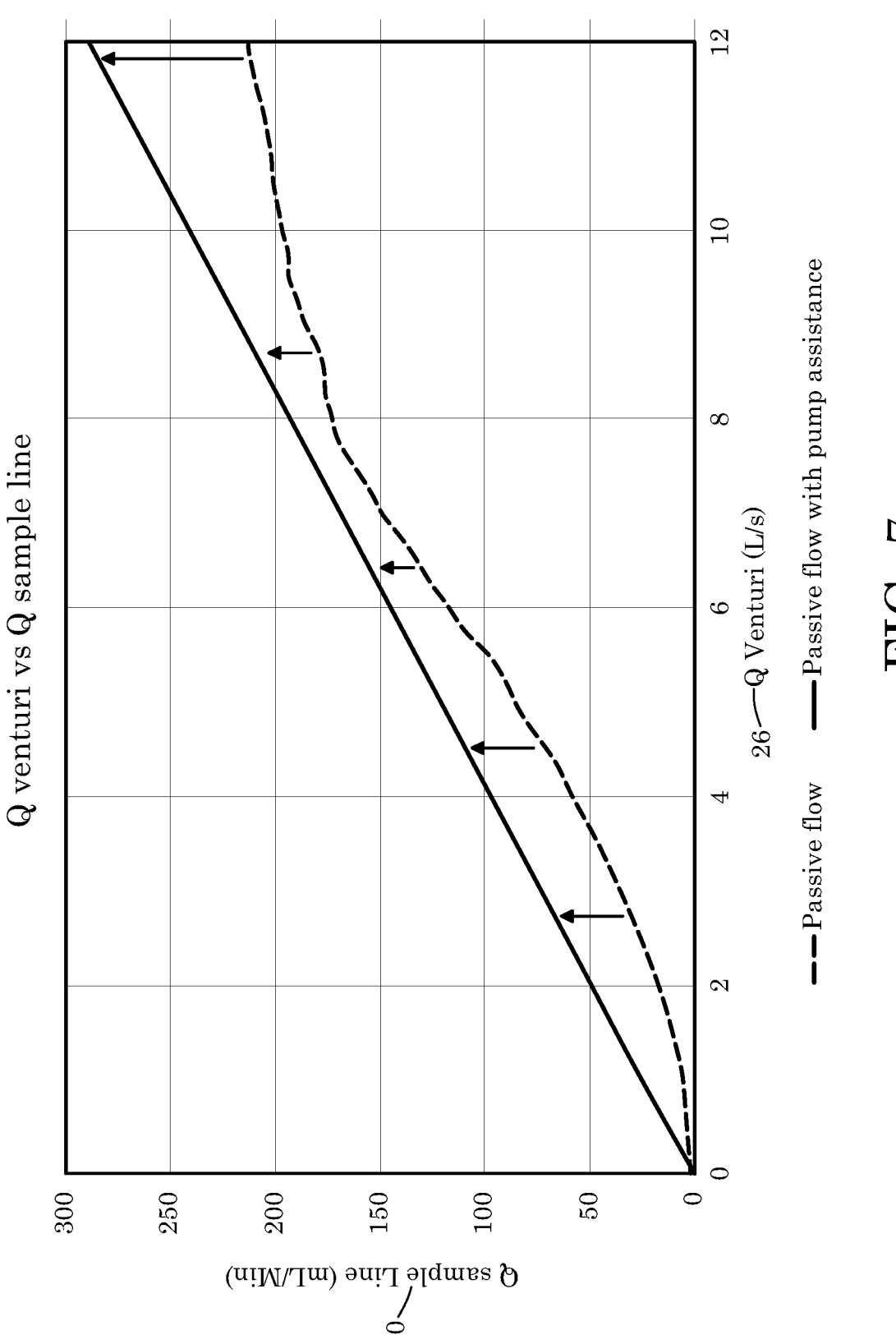
FIG. 7 is a graph of an example of flow rates of breaths passing through the sample line of the device of FIG. 1 and obtained only via passive sampling versus corresponding flow rates of breaths passing through the conduit of the device of FIG. 1, together with an example of flow rates of breaths passing through the sample line which are both passively sampled and pump-assisted so as to be proportional to and versus corresponding flow rates of breaths passing through the conduit.

FIG. 7 shows a non-limiting example of purely passive flow rates of portions of exhalations of air through sample line 40 without pump-assistance (labelled as Q Sample Line) versus flow rates of primary portions of the exhalations of air passing through conduit 26 (labelled as Q Venturi). As seen in FIG. 7, flow rates through sample line 40 may be non-linear or not perfectly linear to flow rates through conduit 26. FIG. 7 also shows a non-limiting example of passive flow through the sample line with assistance from pump 58. Processor 62 of device 20 as herein described is configured to take any passive waveform shape and related data thereof and adjust operation of pump 58 seen in FIG. 2 to transfer achieve a linear relationship of y=kx+b where k is the slope (sample line flow rate 28B versus conduit flow rate 28A) and b is the initial offset. The pump via the processor is configured to dynamically correct the sample flow rate by changing its power to match the chosen slope. Ideally b=0 and the flow through sample line 40 is completely proportional to the flow through conduit. However, processor 62 is configured to both achieve via the pump a proportional relationship between the flow rate of sample portion 28B of exhalation of air 28 through sample line 40 and the flow rate of primary portion 28A of the exhalation of air passing through conduit 26, as well as create a linear relationship between these flows with an initial offset. The pump in this example is configured to increase the flow rate of the exhalation of air passing through the sample line to be linear to the flow rate of the exhalation of air passing through the conduit within a predetermined threshold as seen in FIG. 7.

Referring to FIG. 2, pump 58 thus increases the flow rates of portions 28B of exhalations of air 28 passing through sample line 40 so as to be linear/proportional within a predetermined threshold to the flow rates of primary portions 28A of the exhalation of passing through conduit 26. The pump and processor 62 are configured to adjust and/or increase the flow rate through the sample line until a slope formed by the flow rate of said exhalation of air through the sample line versus the flow rate of said exhalation of air through the conduit, is constant within a predetermined threshold. Pump 58 may be configured to increase the flow rate until a target said slope is obtained within a predetermined threshold.

Passive sampling via the pressure differential results in a passive base said flow rate of the exhalation of air passing through sample line 40, with the pump being configured to supplement the passive said base flow rate of said sampling. Gas sensors 46 are configured to receive sample portion 28B of exhalation of air 28 via the pressure differential caused by restriction 44, with power requirements on pump 58 thus being inhibited. The pressure differential, which enables or facilitates the passive sampling, functions to reduce the power otherwise needed by the pump. Power savings thus result due to the addition of the passive flow. Based on the passive flow design of device 20, the assisted flow can be increased further saving more power. The device so configured, with its passive sampling with enhancement of the flow rate through sample line via pump 58, enables the pump to operate via a smaller battery 64 and/or power source. The pump in one example is configured to minimally adjust the flow rate through sample line 40 so as promote maximum life of the battery.

Figure 8:
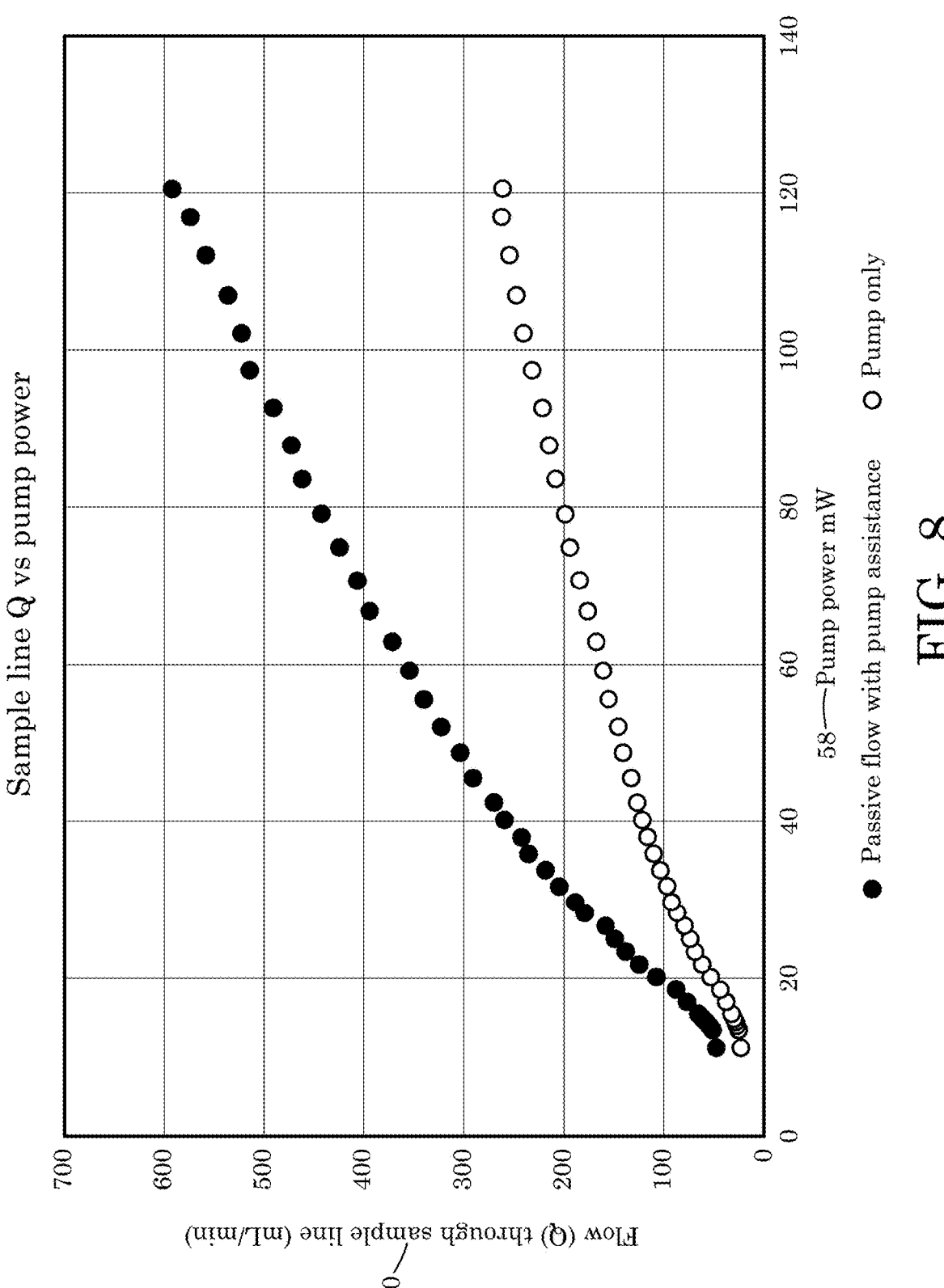
FIG. 8 is a graph of an example of flow rates of breaths passing through the sample line of the device of FIG. 1 which are both passively sampled and pump-assisted versus the corresponding power consumed by the pump, together with an example of flow rates of breaths passing through the sample line in which only pump power is used versus the corresponding power consumed by the pump, with power savings through use of a combination of passive sampling and pump-assistance thus being illustrated.

FIG. 8 shows a non-limiting example of flow rates of portions 28B of exhalations of air passing through sample line 40 where pump 58 is used on its own, versus pump power required to achieve said flow rates. FIG. 8 also shows a non-limiting example of flow rates of the portions of exhalations of air passing through the sample line obtained via both passive sampling and pump assistance. FIG. 8 illustrates that the device, and/or conduit 26 thereof seen in FIG. 2, are thus configured to reduce the power otherwise needed by the pump to maintain a given flow rate of portion 28B of exhalation of air 28 through sample line 40. Referring back to FIG. 8, in this example the power requirements for a given flow rate may be reduced by at least 10 to 15% in one example, may be reduced by 10% or more in another example, may be reduced by at least 10% to 50% in a further example, and may be reduced by 50% or more in yet an additional example. However, these ranges are not strictly required and power savings may be less than or greater than these amounts in other embodiments.

Referring to FIG. 2, pump 58 is configured to selectively operate in a first or breath-mixing mode, which may also be referred to as a mini-mixing chamber mode. The pump in the breath-mixing mode in one example is configured via processor 62 to adjust the flow rate of sample portion 28B of exhalation of air 28 through sample line 40 such that the volume of exhaled air passing into gas sampling chamber 54 per said exhalation of air is less than volume $V_C$ of gas sampling chamber 54. Pump 58 may thus be selectively configured to adjust the flow rate through sample line 40 such that sample portions 28B from multiple exhalations of air 28 are mixed together within the gas sampling chamber. The pump so configured in the breath-mixing mode promotes the mixing of samples of multiple breathes or exhalations of air together within gas sampling chamber 54. A plurality of samples of said one or more exhalations of air are thus mixed together within the gas sampling chamber in the breath-mixing mode.

Figure 9:
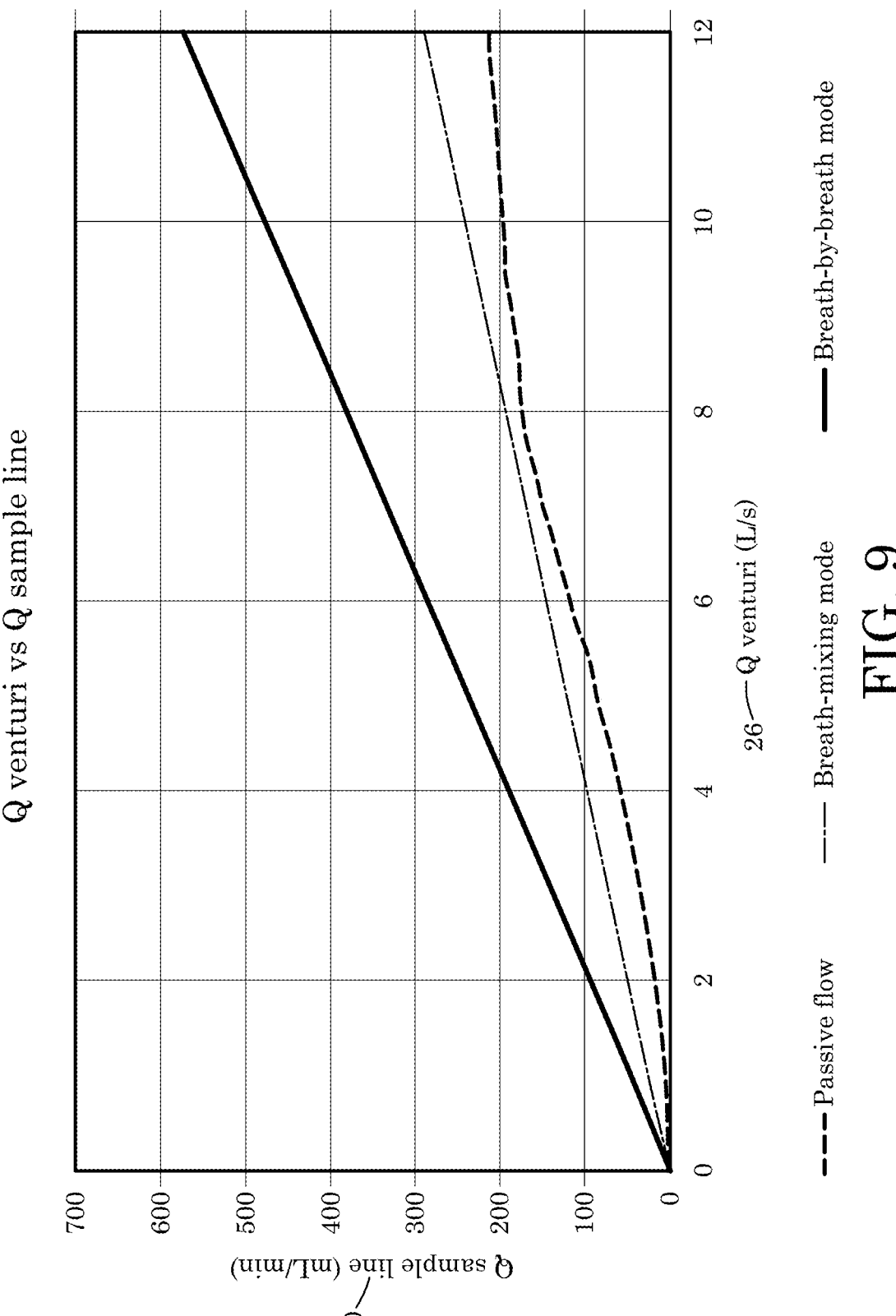
FIG. 9 is a graph of a first example of flow rates of breaths passing through the sample line of the device of FIG. 1 which are obtained only via passive sampling versus corresponding flow rates of breaths passing through the conduit of the device of FIG. 1, a second example of flow rates of breaths passing through the sample line which are passively sampled with pump assistance so as to be proportional to and versus corresponding flow rates of breaths passing through the conduit, with the second example providing minimal pump assistance such that the device operates in a breath-mixing mode in which same portions of successive breaths are mixed together, and a third example of flow rates of breaths passing through the sample line which are passively sampled with pump assistance so as to be proportional to and versus corresponding flow rates of breaths passing through the conduit, with the third example increasing pump assistance compared to the second example such that the device now operates in a breath-by-breath mode in which the gas sampling chamber of the device of FIG. 1 is purged such that oximetry waveforms and/or capnography waveforms may be observed within successive breaths.

In the breath-mixing mode, the pump power curve may be minimal to create a proportional/linear relationship that has flow rates of portions 28B of exhalations of air 28 which result in a sample volume per breath or exhalation of air that is less than the volume $V_C$ of gas sampling chamber 54. In the breath-mixing mode, pump 58 may operate at a minimum power level needed to increase the flow rate of the sample portion of the exhalation of air passing through sample line 40 so as to be proportional/linear to the flow rate of primary portions 28A of the exhalation of air through conduit 26. The pump in this mode and in one example is configured to adjust the flow rate through the sample line such that the slope formed by the flow rate of said exhalation of air through the sample line versus the flow rate of said exhalation of air through the conduit, is minimised as shown in FIG. 9.

This mixing of samples of exhalations of air when pump 58 is in the breath-mixing mode, may function to increase the accuracy of the measurements at gas sensors 46 seen in FIG. 2. The breath-mixing mode may also maximize life of battery 64 seen in FIG. 4. On the other hand, the breath-mixing mode may flatten the waveforms as measured at the gas sensors—similar to what sensors in a mixing-chamber style lab cart might see—thus making it difficult if not impossible to measure oximetry waveforms and/or capnography waveforms in this configuration.

Referring back to FIG. 2, pump 58 is configured to also selectively operate in a second mode, in this example a breath-by-breath mode. In the breath-by-breath mode, the flow rate of the portion 28B of exhalation of air 28 passing through sample line 40 is increased via the pump with gas sampling chamber 54 being purged multiple times per breath or respective said exhalation of air 28 such that oximetry waveforms and/or capnography waveforms may be observed within successive breaths. In the breath-by-breath mode, to capture accurate oximetry waveforms and/or capnography waveforms, it may be important to accurately measure the minima and maxima as these derived values are also used and reported: end-tidal carbon dioxide (ETCO2), end-tidal oxygen (ETO2) and several derivations thereof like end-tidal oxygen tension (PETO2), which is the percent gas concentration converted back to partial pressure of air, and end-tidal carbon dioxide tension (PETCO2) for example. To accurately make these measures and in one example, device 20 in the breath-by-breath mode is configured to purge the sample line and chambers in front of the sensors many times per breath.

Pump 58 in one example of the breath-by-breath mode may be selectively configured via processor 62 to adjust/increase the flow rate through sample line such that the volume of exhaled air passing into the gas sampling chamber per said exhalation of air is multiple times greater than the volume $V_C$ of gas sampling chamber 54. The pump may thus be selectively configured via the processor to increase the flow rate through sample line 40 so as to fully purge gas sampling chamber 54 between respective said exhalations of air 28. Pump 58 may therefore be configured to adjust the flow rate through the sample line such that an initial said exhalation of air through the sample line is purged by a subsequent said exhalation of air through the sample line such that oximetry waveforms and/or capnography waveforms may be observed within successive breaths. The pump may therefore be configured to adjust the flow rate through the sample line so as to inhibit residual air between adjacent said exhalations of air and also enable measurement oximetry waveforms and/or capnography waveforms.

Thus, in the breath-by-breath mode the slope (sample line flow rate 28B—labelled as Q Sample Line, versus conduit flow rate 28A—labelled as Q Venturi) of the pump flow curve is increased as seen in FIG. 9 to facilitate measurement of oximetry waveforms and/or capnography waveforms. The flow rate needed for this operation, while ensuring that the device remains portable, may only able to be reached by using a combination of the passive flow baseline obtained from passive sampling together with pump assistance, thereby reducing the overall power needed by pump 58 seen in FIG. 2 to effectively purge gas sampling chamber 54 between exhalations of air 28. The breath-by-breath mode of operation may thus enable oximetry waveforms and/or capnography waveforms to be captured accurately.

Pump 58 of device 20 as herein described is thus selectively adjustable via processor 62 seen in FIG. 2 so that the flow rate of sample portion 28B of exhalation of air 28 through sample line 40 is such that the volume of exhaled air passing into gas sampling chamber 54 per said exhalation of air is either less than, equal to or greater than volume $V_C$ of the gas sampling chamber.

The device as herein described is configured to selectively change from a breath-mixing mode to a breath-by-breath mode by increasing the ratio of the pump flow rate to the flow rate through conduit 26. Device 20 is thus configured to operate via both breath-mixing and breath-by-breath modes using a single flow path, in this example sample line 40. The device as herein described is thus configured to change between the breath-mixing mode and breath-by-breath mode as a function of operation of pump 58. The relationship between pump flow rate and exhaled flow rate changes between the breath-mixing mode and breath-by-breath mode. Device 20 as herein described is configured to selectively change from a breath-mixing mode to a breath-by-breath mode by selectively adjusting via processor 62 the extent to which pump 58 increases the flow rate of the portion 28B of said one or more exhalations of air 28 being passively sampled.

The amount of power reduction/savings of the pump for device 20 as herein described and as shown by way of non-limiting example in FIG. 8, may be a function of and/or be based on the slope of the pump curve shown by way of non-limiting example in FIG. 9. At a minimal slope (sample line flow rate 28B versus conduit flow rate 28A) such as in the breath-mixing mode, the power savings resulting from the device as herein described may be close to or greater than a 50% power savings/reduction. As the slope (sample line flow rate 28B versus conduit flow rate 28A) becomes steeper such as in the breath-by-breath mode, the power savings may be less but may still be needed/beneficial and may comprise at least a 10-15% power savings/reduction for example.

Figure 3:
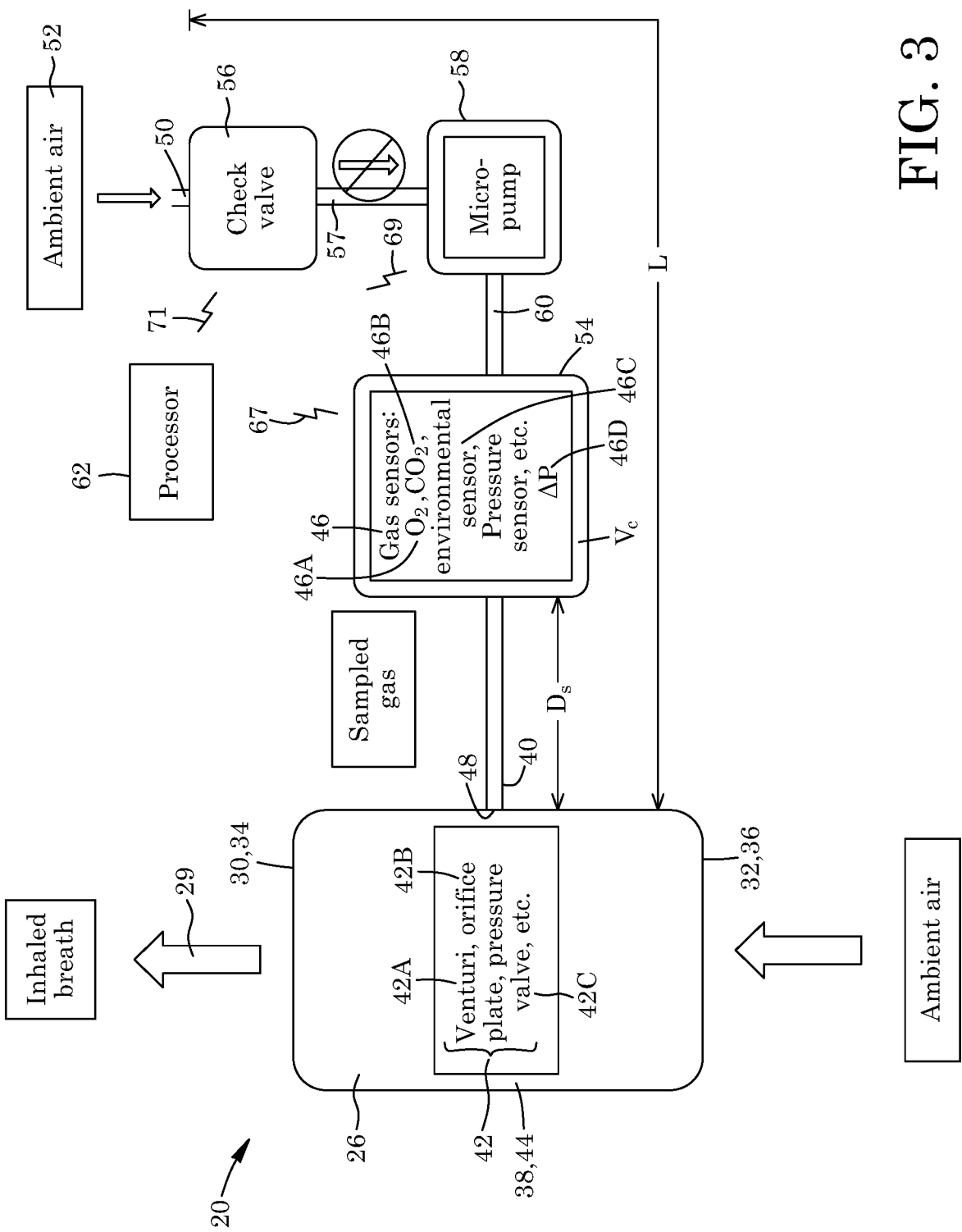
FIG. 3 is a schematic diagram of the device of FIG. 2, showing the flow path of an inhalation of air therethrough.

FIG. 3 illustrates inhalations of air 29 passing through device 20. Processor 62 may be configured to determine breath state via pressure sensor 46D and in response to a determination that an inhalation is occurring, actuate check valve 56 to close. This may function to inhibit backflow through sample line 40. However, it is not strictly required that inhalations of air pass through device 20; rather, only exhaled air is required to pass through conduit 26 of device 20.

There is also provided a method of measuring a person's ventilation and/or metabolism metrics. As seen in FIG. 2, the method includes providing conduit 26 via which primary portion 28A of exhalation of air 28 passes. The method includes in this example positioning at least one and in this example a plurality of gas sensors 46 adjacent the conduit.

The method includes passively sampling a secondary or sample portion 28B of the exhalation of air by means of a positive or negative pressure differential and directing said sample to the gas sensors. The method includes providing means for passive sampling 42 and restriction 44 to create said pressure differential.

The method may include adjusting the flow rate of sample portion 28B of exhalation of air 28 to be proportional to the flow rate of primary portion 28A of the exhalation of air passing through the conduit. The method may include adjusting the flow rate of sample portion 28B of the exhalation of air to achieve linearity within a predetermined threshold to the flow rate of the primary portion of the exhalation of air passing through conduit 26. The method in this example includes providing processor 62 to determine the flow rates of the primary portion 28A of exhalations of air 28 and sample portion 28B of the exhalations of air and to determine the extent which the flow rate of the sample portion of the exhalation of air needs to be increased to achieve proportionality and/or linearity with the primary portion 28A of the exhalation of air passing through conduit 26 within a predetermined threshold.

The method in this example includes providing gas sampling chamber 54 in communication with gas sensors 46. The method may in this example include selectively increasing the flow rate of passively sampled portions 28B of exhalations of air 28 such that the volume of exhaled air passing into the gas sampling chamber per said exhalation of air is less than the volume of the gas sampling chamber in a breath-mixing mode. The method in this example may include selectively increasing the flow rate of passively sampled exhalations of air such that multiple said exhalations of air are mixed together within gas sampling chamber 54.

The method in this example may include selectively increasing the flow rate of passively sampled portions 28B of exhalations of air 28 such that the volume of exhaled air passing into gas sampling chamber 54 per said exhalation of air is multiple times greater than volume $V_C$ of the gas sampling chamber, in a breath-by-breath mode. The method in this example may include selectively increasing the flow rate of passively sampled exhalations of air so as to fully purge the gas sampling chamber between respective said exhalations of air such that oximetry waveforms and/or capnography waveforms may be observed within successive breaths. The method in this example may include selectively increasing the flow rate of passively sampled portions 28B of exhalations of air 28 such that an initial said exhalation of air through sample line 40 is purged by a subsequent said exhalation of air through the sample line so as to facilitate measurement of oximetry waveforms and/or capnography waveforms within successive breaths. The method in this example may include selectively increasing the flow rate of passively sampled exhalations of air so as to inhibit residual air between adjacent said exhalations of air and also enable measurement oximetry waveforms and/or capnography waveforms.

The method in this example may thus include selectively adjusting the flow rate of passively sampled portions 28B of exhalations of air such that the volume of exhaled air passing into the gas sampling chamber per said exhalation of air is less than, equal to or greater than the volume of the gas sampling chamber The method includes using pump 58 and processor 62 to adjust and/or increase the flow rate of the sample portion of the exhalation of air as referred to above. The method includes in this example configuring conduit 26 configured to receive exhalation of air 28 therethrough, passively sampling the exhalation of air by means of a positive or negative pressure differential, and assisting the passive sampling of the exhalation of air via the pump. The method includes configuring pump 58 via processor 62 to supplement a base flow of said passively sampled portion 28B of exhalation of air 28. The method includes lowering power requirements of the pump by relying at least in part on passive sampling of the exhalation of air. The method includes in this example shaping the conduit to reduce power otherwise needed by the pump for sampling purposes by at least 50%.

Many advantages result from the structure of the present invention. Device 20 as herein described enables measurement of a variety of ventilation and/or metabolism metrics including but not limited to carbon dioxide production (VCO2) in addition to existing oxygen consumption (VO2). The addition of VCO2 measurements (capnography) and analysis combined with VO2 analysis may provide users with the ability to collect essential cardiopulmonary data used in shaping key programs in the performance, fitness and wellness sectors that rely on specific substrate analysis (fats, carbs, and protein) and accurate ventilatory threshold detection. VCO2 and VO2 when measured in unison enable the derivation of respiratory exchange ratio (RER), respiratory quotient (RQ), and metabolic substrate utilization in terms of absolute and relative values of fats, carbohydrates, and proteins. The presence of VCO2 increases the accuracy of ventilatory threshold (VT) detection. All these calculations may be relevant to various health, sports and research sectors for example. Device 20 as herein described may enable the delivery of a metabolic analyzer that is portable, affordable, accurate, and easy to use, such that researchers, coaches, gym owners, and athletes may be able to obtain access what is generally accepted as the gold-standard in physiologic assessment: metabolic analysis in cardiopulmonary exercise and at rest for diet management.

Referring to FIG. 2 and as mentioned above, the amount of power needed to increase the flow rate of sample portion 28B of exhalations of air 28 through sample line 40 to gas sensors 46 is reduced due to the passive flow base rate. This reduction in the power needed allows for device 20 to use a power source or battery 64 (seen in FIG. 4) that is relatively small. This further reduces the overall size of device 20. The reduction of power may also substantially increase life of the battery, thus enabling smaller batteries and enabling a pump-assisted sampling device entirely situated on the face. Device 20 is thus able to be an entirely face/head worn metabolic analyzer. The device can also utilize the passive flow with pump 58 to maximize the flow rate through sample line 40 changing the device operation from the breath-mixing mode to the breath-by-breath mode. Doing so with pump 58 alone may be unachievable with a sufficient battery life of two hours minimum.

Additionally and referring back to FIG. 2, the relatively short length L of sample line 40 and distance of separation $D_S$ to gas sensors 46 may increase the accuracy in the gas alignment as distance traveled between the main flow or primary portion 28A of exhalation of air 28 and gas sensors 46 is minimal. The sample line so sized may increase the accuracy in the VO2/VCO2 measurements because of the time-domain alignment of the flow and gas concentration. Gas sensors 46 of device 20 as herein described and so configured may measure the concentrations of the gas more accurately to the instantaneous flow (Q) of the venturi. VO2 and VCO2 are calculated from two parameters, the first being ventilation of the subject and the second being the gas concentrations of the exhaled breath. The calculations are only accurate when the two parameters are time aligned.

Figure 10:
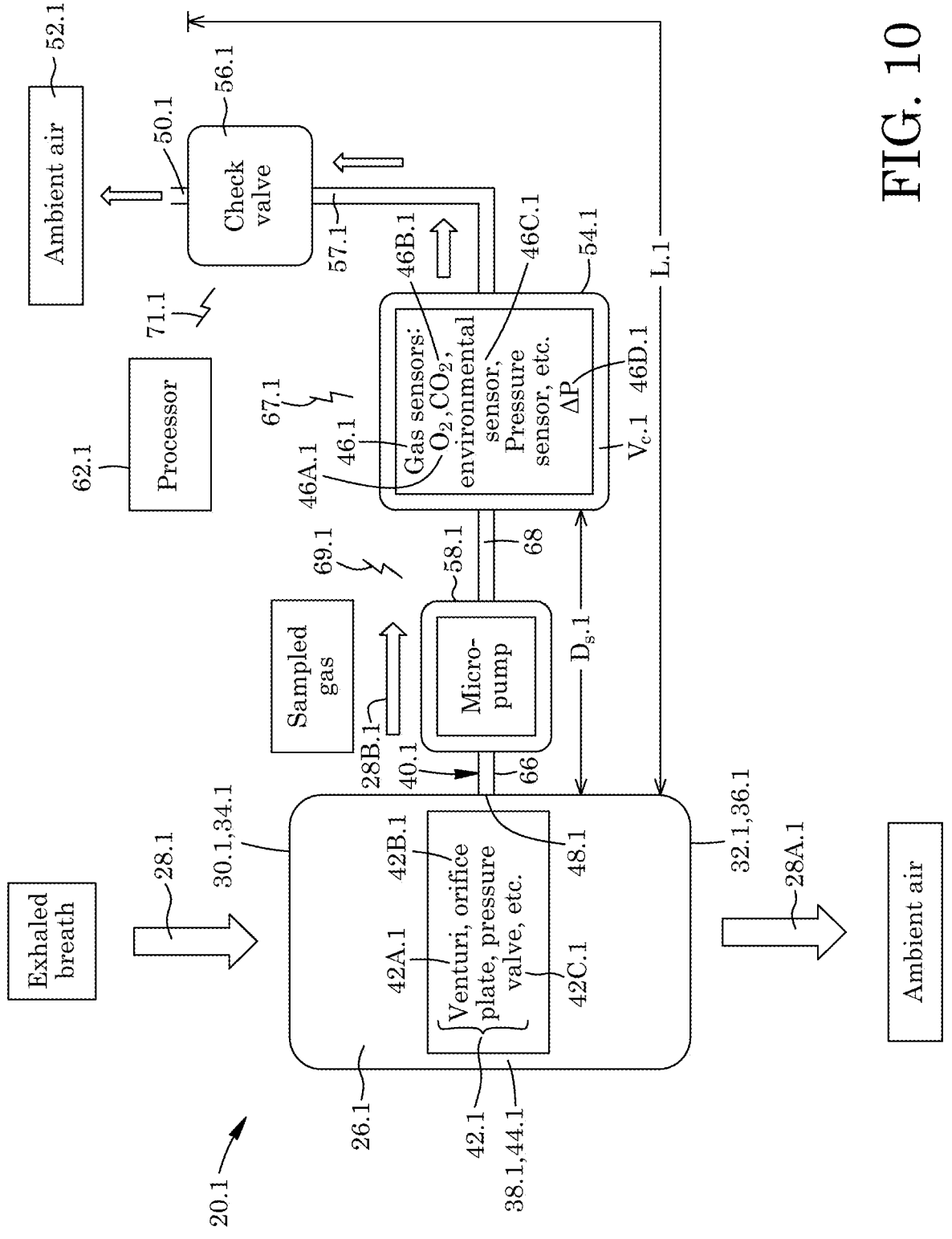
FIG. 10 is a schematic diagram of a device for measuring a person's ventilation or metabolism metrics according to another aspect, showing the flow path of an exhalation of air passing through a conduit thereof, with a portion of the exhalation of air passing through a sample line to one or more gas sensors within a gas sampling chamber, with the portion of the exhalation of air being obtained via passive sampling with supplementary pump assistance.
Figure 11:
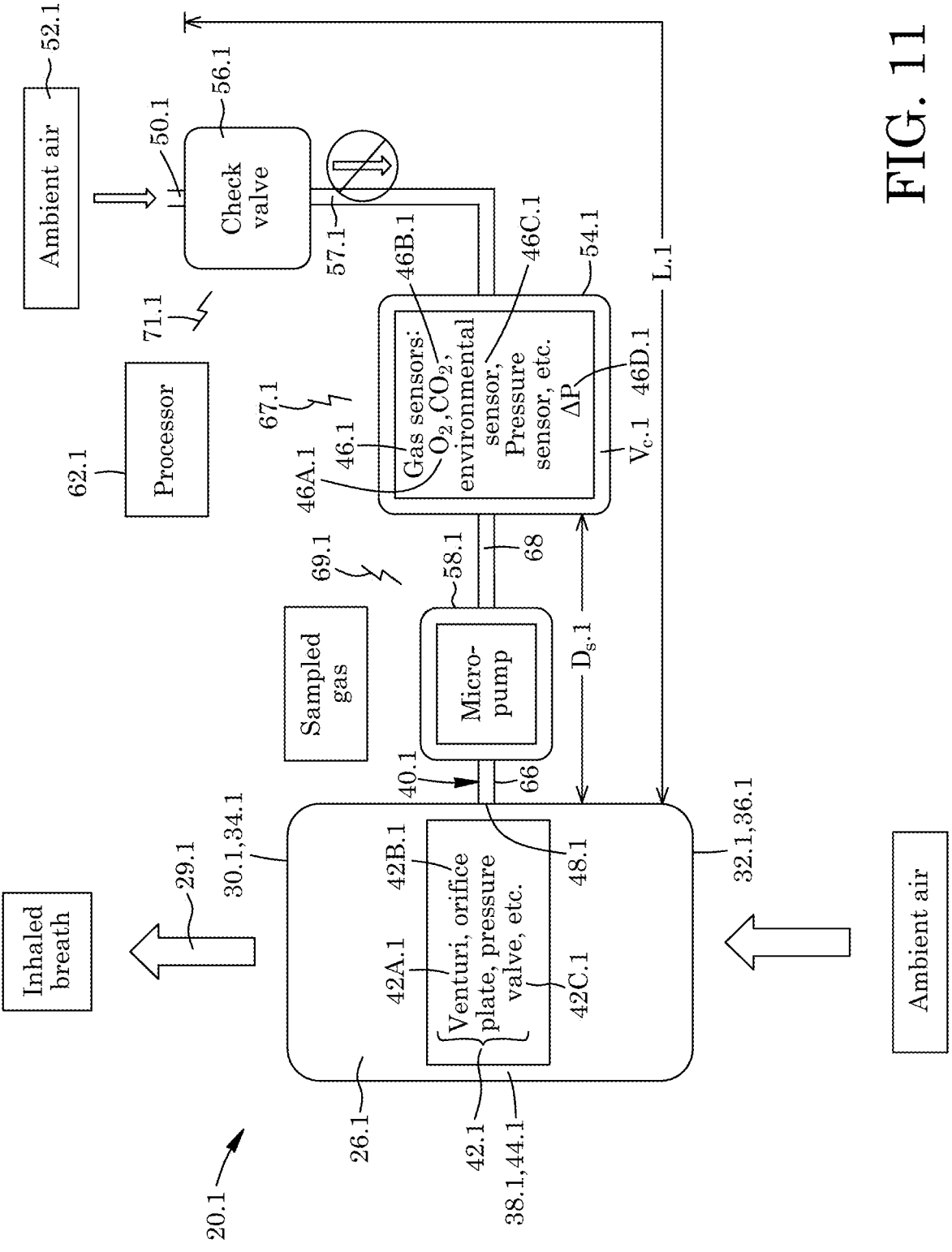
FIG. 11 is a schematic diagram of the device of FIG. 10, showing the flow path of an inhalation of air therethrough.

FIGS. 10 to 11 show a device 20.1 for measuring a person's ventilation and/or metabolism metrics according to another aspect. Like parts have like numbers and functions as the device 20 shown in FIGS. 1 to 9 with the addition of decimal extension "0.1". Device 20.1 is substantially the same as device 20 shown in FIGS. 1 to 9 with at least the following exceptions.

As seen in FIG. 10, pump 58.1 is upstream of gas sensors 46.1. The pump is in fluid communication with port 48.1 via a passageway, in this example hose 66 of sample line 40.1. Pump 58.1 is in fluid communication with gas sensors 46.1 via a passageway, in this example hose 68 of the sample line. The gas sensors are interposed between the pump and check valve 56.1 in this example.

It will be appreciated that many variations are possible within the scope of the invention described herein. Where a component (e.g. a software module, processor, assembly, device, circuit, etc.) is referred to herein, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

The invention may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In some embodiments, the invention may be implemented in software. For greater clarity, "software" includes any instructions executed on a processor, and may include (but is not limited to) firmware, resident software, microcode, code for configuring a configurable logic circuit, applications, apps, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Software and other modules may reside on servers, workstations, personal computers, tablet computers, and other devices suitable for the purposes described herein.

INTERPRETATION OF TERMS

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms. These terms ("a", "an", and "the") mean one or more unless stated otherwise;

"and/or" is used to indicate one or both stated cases may occur, for example A and/or B includes both (A and B) and (A or B);

"approximately" when applied to a numerical value means the numerical value ±10%;

where a feature is described as being "optional" or "optionally" present or described as being present "in some embodiments" it is intended that the present disclosure encompasses embodiments where that feature is present and other embodiments where that feature is not necessarily present and other embodiments where that feature is excluded. Further, where any combination of features is described in this application this statement is intended to serve as antecedent basis for the use of exclusive terminology such as "solely," "only" and the like in relation to the combination of features as well as the use of "negative" limitation(s)" to exclude the presence of other features; and "first" and "second" are used for descriptive purposes and cannot be understood as indicating or implying relative importance or indicating the number of indicated technical features.

Words that indicate directions such as "vertical", "transverse", "horizontal", "upward", "downward", "forward", "backward", "inward", "outward", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Where a range for a value is stated, the stated range includes all sub-ranges of the range. It is intended that the statement of a range supports the value being at an endpoint of the range as well as at any intervening value to the tenth of the unit of the lower limit of the range, as well as any subrange or sets of sub ranges of the range unless the context clearly dictates otherwise or any portion(s) of the stated range is specifically excluded. Where the stated range includes one or both endpoints of the range, ranges excluding either or both of those included endpoints are also included in the invention.

Certain numerical values described herein are preceded by "about". In this context, "about" provides literal support for the exact numerical value that it precedes, the exact numerical value ±5%, as well as all other numerical values that are near to or approximately equal to that numerical value. Unless otherwise indicated a particular numerical value is included in "about" a specifically recited numerical value where the particular numerical value provides the substantial equivalent of the specifically recited numerical value in the context in which the specifically recited numerical value is presented. For example, a statement that something has the numerical value of "about 10" is to be interpreted as: the set of statements:

in some embodiments the numerical value is 10;

in some embodiments the numerical value is in the range of 9.5 to 10.5;

and if from the context the person of ordinary skill in the art would understand that values within a certain range are substantially equivalent to 10 because the values with the range would be understood to provide substantially the same result as the value 10 then "about 10" also includes:

in some embodiments the numerical value is in the range of C to D where C and D are respectively lower and upper endpoints of the range that encompasses all of those values that provide a substantial equivalent to the value 10

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

As will be apparent to those of skill in the art upon reading this disclosure, each of the individual embodiments described and illustrated herein has discrete components and features which may be readily separated from or combined with the features of any other described embodiment(s) without departing from the scope of the present invention.

Any aspects described above in reference to apparatus may also apply to methods and vice versa.

Any recited method can be carried out in the order of events recited or in any other order which is logically possible. For example, while processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, simultaneously or at different times.

Various features are described herein as being present in "some embodiments". Such features are not mandatory and may not be present in all embodiments. Embodiments of the invention may include zero, any one or any combination of two or more of such features. All possible combinations of such features are contemplated by this disclosure even where such features are shown in different drawings and/or described in different sections or paragraphs. This is limited only to the extent that certain ones of such features are incompatible with other ones of such features in the sense that it would be impossible for a person of ordinary skill in the art to construct a practical embodiment that combines such incompatible features. Consequently, the description that "some embodiments" possess feature A and "some embodiments" possess feature B should be interpreted as an express indication that the inventors also contemplate embodiments which combine features A and B (unless the description states otherwise or features A and B are fundamentally incompatible). This is the case even if features A and B are illustrated in different drawings and/or mentioned in different paragraphs, sections or sentences.

ADDITIONAL DESCRIPTION

Examples of devices for measuring a person's ventilation or metabolism metrics have been described. The following clauses are offered as further description.

(1) A device for measuring a person's ventilation or metabolism metrics, the device comprising: a conduit shaped to receive an exhalation of air therethrough; at least one gas sensor in fluid communication with the conduit and configured to passively sample the exhalation of air by means of a positive or negative pressure differential; and a pump configured to adjust the flow rate of the sample of said exhalation of air passing through the sample line so as to be proportional within a predetermined threshold, to the flow rate of the exhalation of air passing through the conduit.

(2) A device according to clause 1, or any preceding or subsequent clause, wherein the pump is configured to adjust the flow rate through the sample line until a slope formed by the flow rate of said exhalation of air through the sample line versus the flow rate of said exhalation of air through the conduit, is constant within a predetermined threshold.

(3) A device according to clause 1, or any preceding or subsequent clause, wherein the pump is configured to increase the flow rate of the exhalation of air passing through the sample line to until a target slope of said flow rate of the exhalation of air passing through the sample line versus the flow rate of the exhalation of air passing through the conduit, is obtained within a predetermined threshold.

(4) A device according to any one of clauses 1 to 3, or any preceding or subsequent clause, wherein the pump is configured to adjust the flow rate through the sample line such that the slope formed by the flow rate of said exhalation of air through the sample line versus the flow rate of said exhalation of air through the conduit, is minimised.

(5) A device according to any one of clauses 1 to 4, or any preceding or subsequent clause, including a gas sampling chamber in communication with the at least one gas sensor and wherein the pump is configured to adjust the flow rate through the sample line such that the volume of exhaled air passing into the gas sampling chamber per said exhalation of air is less than the volume of the gas sampling chamber.

(6) A device according to any one of clauses 1 to 4, or any preceding or subsequent clause, including a gas sampling chamber in communication with the at least one gas sensor and wherein the pump is configured to adjust the flow rate through the sample line such that multiple said exhalations of air are mixed together within the gas sampling chamber.

(7) A device according to any one of clauses 1 to 6, or any preceding or subsequent clause, including a battery to power the at least one gas sensor and the pump, and wherein the pump is configured to minimally adjust the flow rate through the sample line so as promote maximum life of said battery.

(8) A device according to any one of clauses 1 to 4, or any preceding or subsequent clause, including a gas sampling chamber in communication with the at least one gas sensor and wherein the pump is configured to adjust the flow rate through the sample line such that the volume of exhaled air passing into the gas sampling chamber per said exhalation of air is generally or substantially equal to the volume of the gas sampling chamber.

(9) A device according to any one of clauses 1 to 4, or any preceding or subsequent clause, including a gas sampling chamber in communication with the at least one gas sensor, wherein the pump is configured to adjust the flow rate through the sample line such that the volume of exhaled air passing into the gas sampling chamber per said exhalation of air is greater than the volume of the gas sampling chamber.

(10) A device according to any one of clauses 1 to 4, or any preceding or subsequent clause, including a gas sampling chamber in communication with the at least one gas sensor and wherein the pump is configured to increase the flow rate through the sample line so as to fully purge the gas sampling chamber between respective said exhalations of air.

(11) A device according to any one of clauses 8 to 10, or any preceding or subsequent clause, wherein the pump is configured to adjust the flow rate through the sample line such that an initial said exhalation of air through the sample line is purged by a subsequent said exhalation of air through the sample line.

(12) A device according to any one of clauses 8 to 11, or any preceding or subsequent clause, wherein the pump is configured to adjust the flow rate through the sample line so as to inhibit residual air between adjacent said exhalations of air.

(13) A device according to any one of clauses 1 to 4, or any preceding or subsequent clause, including a gas sampling chamber in communication with the at least one gas sensor and wherein the pump is selectively adjustable so that the flow rate through the sample line is such that the volume of exhaled air passing into the gas sampling chamber per said exhalation of air is either less than or greater than the volume of the gas sampling chamber.

(14) A device according to any one of clauses 1 to 4, or any preceding or subsequent clause, including a gas sampling chamber in communication with the at least one gas sensor and wherein the pump is selectively adjustable so that the flow rate through the sample line is such that the volume of exhaled air passing into the gas sampling chamber per said exhalation of air is less than, equal to, or greater than the volume of the gas sampling chamber.

(15) A device according to any one of clauses 1 to 14, or any preceding or subsequent clause, wherein the pump is configured to increase the flow rate of the exhalation of air passing through the sample line to be linear within a predetermined threshold, to the flow rate of the exhalation of air passing through the conduit.

(16) A device according to any one of clauses 1 to 15, or any preceding or subsequent clause, wherein passive sampling via the pressure differential results in a base flow rate of the exhalation of air passing through the sample line, with the pump being configured to supplement the base flow rate of said sampling.

(17) A device according to any one of clauses 1 to 15, or any preceding or subsequent clause, wherein passive sampling via the pressure differential results in a passive base said flow rate of the exhalation of air passing through the sample line, with power requirements on the pump thus being inhibited.

(18) A device according to any one of clauses 1 to 15, or any preceding or subsequent clause, wherein the at least one gas sensor is configured to primarily receive a sample of the exhalation of air via the pressure differential caused by the shape of the conduit, with power requirements on the pump thus being inhibited.

(19) A device according to any one of clauses 1 to 18, or any preceding or subsequent clause, wherein the pressure differential functions to reduce the power otherwise needed by the pump.

(20) A device according to any one of clauses 17 to 19, or any preceding or subsequent clause, wherein the conduit is configured to reduce the power otherwise needed by the pump to maintain the flow rate through the sample line by 10% or more.

(21) A device according to any one of clauses 17 to 20, or any preceding or subsequent clause, wherein the conduit is configured to reduce the power otherwise needed by the pump to maintain the flow rate through the sample line by at least 10% to 50%.

(22) A device according to any one of clauses 17 to 21, or any preceding or subsequent clause, wherein the conduit is configured to reduce the power otherwise needed by the pump to maintain the flow rate through the sample line by 50% or more.

(23) A device according to any one of clauses 17 to 22, or any preceding or subsequent clause, wherein the conduit is configured to reduce the power otherwise needed by the pump to maintain the flow rate through the sample line such that battery life of the device is at least equal to or greater than two hours.

(24) A device according to any one of clauses 1 to 23, or any preceding or subsequent clause, wherein passive sampling via the pressure differential results in a passive base said flow rate of the exhalation of air passing through the sample line, thereby enabling the pump to operate via a smaller battery source.

(25) A device according to any one of clauses 1 to 24, or any preceding or subsequent clause, wherein the battery is portable.

(26) A device according to any one of clauses 1 to 25, or any preceding or subsequent clause, wherein the battery is a AA-type battery, AAA-type battery or similar such battery.

(27) A device according to any one of clauses 1 to 26, or any preceding or subsequent clause, wherein the pump is a micro-fluid pump.

(28) A device according to any one of clauses 1 to 27, or any preceding or subsequent clause, wherein the pump weighs five grams or less.

(29) A device according to any one of clauses 1 to 28, or any preceding or subsequent clause, wherein the pump has a form factor of approximately equal to or less than 3 centimeters by 2 centimeters.

(30) A device according to any one of clauses 1 to 29, or any preceding or subsequent clause, wherein the pump has a form factor of approximately equal to or less than 3 centimeters by 1 centimeters.

(31) A device according to any one of clauses 1 to 30, or any preceding or subsequent clause, wherein the length of the sample line is equal to or less than 10 inches.

(32) A device according to any one of clauses 1 to 31, or any preceding or subsequent clause, wherein the at least one gas sensor is adjacent to the conduit.

(33) A device according to any one of clauses 1 to 32, or any preceding or subsequent clause, wherein the device is configured to inhibit the distance of separation between the conduit and the at least one gas sensor.

(34) A device according to any one of clauses 1 to 33, or any preceding or subsequent clause, wherein the at least one gas sensor comprises an oxygen sensor.

(35) A device according to clause 34, or any preceding or subsequent clause, wherein the oxygen sensor comprises a galvanic said oxygen sensor.

(36) A device according to any one of clauses 1 to 35, or any preceding or subsequent clause, wherein the at least one gas sensor comprises a carbon dioxide ($CO_2$) sensor.

(37) A device according to clause 36, or any preceding or subsequent clause, wherein the carbon dioxide ($CO_2$) sensor comprises a nondispersive infrared (NDIR) said $CO_2$ sensor.

(38) A device according to any one of clauses 1 to 37, or any preceding or subsequent clause, wherein the at least one gas sensor comprises a flow sensor.

(39) A device according to any one of clauses 1 to 38, or any preceding or subsequent clause, wherein the at least one gas sensor comprises a pressure sensor.

(40) A device according to any one of clauses 1 to 39, or any preceding or subsequent clause, wherein the at least one gas sensor comprises a differential pressure sensor.

(41) A device according to any one of clauses 38 to 40, or any preceding or subsequent clause, wherein the flow or pressure sensor is used to determine breath state or flow rate.

(42) A device according to any one of clauses 38 to 41, or any preceding or subsequent clause, wherein the flow or pressure sensor is used to determine the flow rate of the sample of said exhalation of air passing through the sample line.

(43) A device according to any one of clauses 1 to 42, or any preceding or subsequent clause, wherein the at least one gas sensor comprises an environmental sensor.

(44) A device according to any one of clauses 1 to 43, or any preceding or subsequent clause, including a connector shaped to selectively couple to a facemask.

(45) A device according to any one of clauses 1 to 44, or any preceding or subsequent clause, wherein the device is shaped and sized to be face-mounted and/or head-worn.

(46) A device according to any one of clauses 1 to 45, or any preceding or subsequent clause, wherein the device is a wearable said device.

(47) A device according to any one of clauses 1 to 46, or any preceding or subsequent clause, wherein the device is configured to be portable.

(48) A device according to any one of clauses 1 to 47, or any preceding or subsequent clause, wherein the device is configured to determine the volume of consumed oxygen (VO2) in said exhalation of air.

(49) A device according to any one of clauses 1 to 48, or any preceding or subsequent clause, wherein the device is configured to determine the volume of expired carbon dioxide (VCO2) in said exhalation of air.

(50) A device according to any one of clauses 1 to 49, or any preceding or subsequent clause, including a processor configured to receive flow rate data for the conduit and the sample line, determine the extent to which the flow rate of the portion of said exhalation of air passing through the sample line must be increased to achieve proportionality between the flow rates within a predetermined threshold and actuating the pump based on the same.

(51) A device according to any one of clauses 1 to 50, or any preceding or subsequent clause, including a processor configured to receive flow rate data for the conduit and the sample line, determine the extent to which the flow rate of the portion of said exhalation of air passing through the sample line must be increased to achieve linearity between the flow rates within a predetermined threshold and actuating the pump based on the same.

(52) A device according to any one of clauses 1 to 50, or any preceding or subsequent clause, including a processor configured to determine the volume of consumed oxygen (VO2) and the volume of expired carbon dioxide (VCO2) based on ventilation and the gas concentration of said exhalation of air which are time aligned.

(53) A device according to any one of clauses 1 to 52, or any preceding or subsequent clause, wherein the device is configured to determine minute ventilation.

(54) A device according to any one of clauses 1 to 53, or any preceding or subsequent clause, wherein the device is configured to determine respiratory frequency (Rf).

(55) A device according to any one of clauses 1 to 54, or any preceding or subsequent clause, wherein the device is configured to determine tidal volume (Tv).

(56) A device according to any one of clauses 1 to 55, or any preceding or subsequent clause, wherein the device is configured to determine one or more of: a fraction of expired oxygen (FeO2); and a fraction of expired carbon dioxide (FeCO2).

(57) A device according to any one of clauses 1 to 56, or any preceding or subsequent clause, wherein the device is configured to determine one or more of: a fraction of inspired oxygen (FiO2); and fraction of inspired carbon dioxide (FiCO2).

(58) A device according to any one of clauses 1 to 57, or any preceding or subsequent clause, wherein the device is configured to determine or quantify one or more aspects of a person's ventilation or metabolism metrics.

(59) A device according to any one of clauses 1 to 58, or any preceding or subsequent clause, wherein the pump is upstream of the at least one gas sensor.

(60) A device according to any one of clauses 1 to 59, or any preceding or subsequent clause, wherein the pump is downstream of the at least one gas sensor.

(61) A device according to any one of clauses to 1 to 60, or any preceding or subsequent clause, including a one-way valve downstream of the at least one gas sensor.

(62) A device according to any one of clauses to 1 to 60, or any preceding or subsequent clause, including a one-way valve downstream of the pump.

(63) A device according to any one of clauses 1 to 60, or any preceding or subsequent clause, wherein the pump includes a one-way valve therewithin and/or as a part thereof.

(64) A device according to any one of clauses 1 to 63, or any preceding or subsequent clause, including a restriction configured to promote flow of a portion of the exhalation of air through said sample line to the at least one gas sensor.

(65) A device for measuring a person's ventilation or metabolism metrics, the device comprising: a conduit shaped to receive an exhalation of air therethrough; at least one gas sensor in communication with the conduit via a sample line; a restriction within the conduit and configured to promote flow of a portion of the exhalation of air through said sample line to the at least one gas sensor; and a pump configured to adjust the flow rate through the sample line to the at least one gas sensor to promote a flow rate through the sample line that is proportional within a predetermined threshold, to the exhalation of air passing through the conduit.

(66) A device according to any one of clauses 64 to 65, or any preceding or subsequent clause, wherein the conduit is a venturi tube and wherein the restriction is a constriction.

(67) A device according to any one of clauses 64 to 66, or any preceding or subsequent clause, wherein the conduit has a first end portion and a second end portion spaced-apart from the first end portion thereof, and wherein the restriction comprises an intermediate portion of the conduit between the end portions of the conduit, the intermediate portion of the conduit having a cross-sectional area less than at least one of the first end portion and the second end portion of the conduit.

(68) A device according to any one of clauses 64 to 65, or any preceding or subsequent clause, wherein the restriction comprises an orifice plate with a side stream said sample line in fluid communication therewith.

(69) A device according to any one of clauses 64 to 65, or any preceding or subsequent clause, wherein the restriction comprises a pressure valve.

(70) A device for measuring a person's ventilation or metabolism metrics, the device comprising: a conduit shaped to receive an exhalation of air therethrough; and at least one gas sensor passively sampling said exhalation of air by means of a positive or negative pressure differential; and a pump configured to assist in said passive sampling.

(71) A device for measuring a person's ventilation or metabolism metrics, the device comprising: a conduit through which an exhalation of air passes, the conduit being configured to create a pressure differential therewithin; a gas sampling chamber; a gas sensor in communication with the gas sampling chamber and the conduit via a sample line, the gas sensor being supplied the exhalation of air by means of positive or negative said pressure differential; and a pump configured to increase the flow rate through the sample line to the at least one gas sensor such that the volume of exhaled air passing into the gas sampling chamber per said exhalation of air is less than the volume of the gas sampling chamber.

(72) A device for measuring a person's ventilation or metabolism metrics, the device comprising: a conduit through which an exhalation of air passes, the conduit being configured to create a pressure differential therewithin; a gas sampling chamber; a gas sensor in communication with the gas sampling chamber and the conduit via a sample line, the gas sensor being supplied the exhalation of air by means of positive or negative said pressure differential; and a pump configured to increase the flow rate through the sample line to the at least one gas sensor such that the volume of exhaled air passing into the gas sampling chamber per said exhalation of air equal to the volume of the gas sampling chamber.

(73) A device for measuring a person's ventilation or metabolism metrics, the device comprising: a conduit through which an exhalation of air passes, the conduit being configured to create a pressure differential therewithin; a gas sampling chamber; a gas sensor in communication with the gas sampling chamber and the conduit via a sample line, the gas sensor being supplied the exhalation of air by means of positive or negative said pressure differential; and a pump configured to increase the flow rate through the sample line to the at least one gas sensor such that the volume of exhaled air passing into the gas sampling chamber per said exhalation of air is greater than the volume of the gas sampling chamber.

(74) A device for measuring a person's ventilation or metabolism metrics, the device comprising: a conduit with a pressure differential being formed with exhaled air passing therethrough; at least one gas sensor in fluid communication with the conduit via a sample line and using passive flow to direct exhaled air to the at least one gas sensor; and a pump which dynamically adjusts flow of said exhaled air through the sample line to the at least one gas sensor such that a sample line said flow rate is proportional within a predetermined threshold, to a primary said flow rate passing through the conduit.

(75) A method of measuring a person's ventilation or metabolism metrics, the method comprising: providing a conduit via which a primary portion of an exhalation of air passes; passively sampling a secondary portion of the exhalation of air by means of a positive or negative pressure differential and directing said sample to at least one gas sensor; and adjusting the flow rate of the secondary portion of the exhalation of air to be proportional within a predetermined threshold, to the flow rate of the primary portion of the exhalation of air passing through the conduit.

(76) A method according to clause 75, or any preceding or subsequent clause, including adjusting the flow rate of the secondary portion of the exhalation of air to achieve linearity within said predetermined threshold to the flow rate of the primary portion of the exhalation of air passing through the conduit.

(77) A method according to any one of clauses 75 to 76, or any preceding or subsequent clause, including providing a processor to determine the flow rates of the primary portion of said exhalation of air and said secondary portion of the exhalation of air and to determine the extent which the flow rate of the secondary portion of the exhalation of air needs to be increased to achieve proportionality with the primary portion of the exhalation of air within said predetermined threshold.

(78) A method according to any one of clauses 75 to 77, or any preceding or subsequent clause, including: providing a gas sampling chamber in communication with the at least one gas sensor; and increasing the flow rate of passively sampled exhalations of air such that the volume of exhaled air passing into the gas sampling chamber per said exhalation of air is less than the volume of the gas sampling chamber.

(79) A method according to any one of clauses 75 to 77, or any preceding or subsequent clause, including: providing a gas sampling chamber in communication with the at least one gas sensor; and increasing the flow rate of passively sampled exhalations of air such that multiple said exhalations of air are mixed together within the gas sampling chamber

(80) A method according to any one of clauses 75 to 77, or any preceding or subsequent clause, including: providing a gas sampling chamber in communication with the at least one gas sensor; and increasing the flow rate of passively sampled exhalations of air such that the volume of exhaled air passing into the gas sampling chamber per said exhalation of air is generally or substantially equal to the volume of the gas sampling chamber.

(81) A method according to any one of clauses 75 to 77, or any preceding or subsequent clause, including: providing a gas sampling chamber in communication with the at least one gas sensor; and increasing the flow rate of passively sampled exhalations of air such that the volume of exhaled air passing into the gas sampling chamber per said exhalation of air is greater than the volume of the gas sampling chamber.

(82) A method according to any one of clauses 75 to 77, or any preceding or subsequent clause, including: providing a gas sampling chamber in communication with the at least one gas sensor; and increasing the flow rate of passively sampled exhalations of air so as to fully purge the gas sampling chamber between respective said exhalations of air.

(83) A method according to any one of clauses 75 to 77, or any preceding or subsequent clause, including: providing a gas sampling chamber in communication with the at least one gas sensor; and increasing the flow rate of passively sampled exhalations of air such that an initial said exhalation of air through the sample line is purged by a subsequent said exhalation of air through the sample line.

(84) A method according to any one of clauses 75 to 77, or any preceding or subsequent clause, including: providing a gas sampling chamber in communication with the at least one gas sensor; and increasing the flow rate of passively sampled exhalations of air so as to inhibit residual air between adjacent said exhalations of air.

(85) A method according to any one of clauses 75 to 77, or any preceding or subsequent clause, including: providing a gas sampling chamber in communication with the at least one gas sensor; and increasing the flow rate of passively sampled exhalations of air such that the volume of exhaled air passing into the gas sampling chamber per said exhalation of air is either less than or greater than the volume of the gas sampling chamber

(86) A method according to any one of clauses 75 to 77, or any preceding or subsequent clause, including: providing a gas sampling chamber in communication with the at least one gas sensor; and increasing the flow rate of passively sampled exhalations of air such that the volume of exhaled air passing into the gas sampling chamber per said exhalation of air is less than, equal to or greater than the volume of the gas sampling chamber.

(87) A method according to any one of clauses 75 to 86, or any preceding or subsequent clause, including positioning the at least one gas sensor adjacent the conduit.

(88) A method according to any one of clauses 75 to 87, or any preceding or subsequent clause, wherein the at least one gas sensor is one or more of an oxygen sensor, a carbon dioxide ($CO_2$) sensor, a flow sensor, a pressure sensor and an environmental sensor.

(89) A method according to clause 88, or any preceding or subsequent clause, wherein the flow or pressure sensor is used to determine breath state or flow rate and/or is used to determine the flow rate of the secondary portion of the exhalation of air.

(90) A method according to any one of clauses 75 to 89, or any preceding or subsequent clause, including using a pump to adjust the flow rate of the secondary portion of the exhalation of air.

(91) A method of measuring a person's ventilation or metabolism metrics, the method comprising: providing a conduit shaped to receive an exhalation of air therethrough; passively sampling the exhalation of air by means of a positive or negative pressure differential; and assisting the passive sampling of the exhalation of air via a pump.

(92) A method according to clause 91, or any preceding or subsequent clause, including directing said sample to at least one gas sensor.

(93) A method according to any one of clauses 90 to 92, or any preceding or subsequent clause, including configuring the pump to supplement a base flow of said passively sampled exhalation of air.

(94) A method according to any one of clauses 90 to 93, or any preceding or subsequent clause, including lowering power requirements of the pump by primarily relying on passive sampling of the exhalation of air.

(95) A method according to any one of clauses 90 to 94, or any preceding or subsequent clause, including shaping the conduit to reduce power otherwise needed by the pump for sampling purposes by at least 50%.

(96) A method according to any one of clauses 90 to 95, or any preceding or subsequent clause, including providing a restriction to create said pressure differential.

(97) A method according to clause 96, or any preceding or subsequent clause, wherein the restriction is one or more of: a constriction in a venturi tube; an intermediate portion of the conduit between end portions of the conduit, with the intermediate portion of the conduit having a cross-sectional area less than at least one of the end portions of the conduit; an orifice plate with a sample line in fluid communication therewith; and a pressure valve.

(98) A device for measuring a person's ventilation or metabolism metrics, the device comprising: a conduit shaped to receive an exhalation of air therethrough; at least one gas sensor in fluid communication with the conduit and configured to passively sample the exhalation of air by means of a positive or negative pressure differential; and wherein the device is configured to operate via both breath-mixing and breath-by-breath modes using a single flow path.

(99) A device according to clause 98, or any preceding or subsequent clause, including a pump which adjusts the flow rate of the portion of the exhalation of air to be passively sampled.

(100) A device according to clause 99, or any preceding or subsequent clause, wherein the device is configured to change between said modes as a function of operation of the pump.

(101) A device for measuring a person's ventilation or metabolism metrics, the device comprising: a conduit shaped to receive one or more exhalations of air therethrough; at least one gas sensor and a gas sampling chamber in fluid communication with the gas sampling chamber and configured to passively sample the one or more exhalations of air by means of a positive or negative pressure differential; and a pump via which the device is configured to selectively change from a breath-mixing mode to a breath-by-breath mode by selectively adjusting the extent to which the pump increases the flow rate of the portion of said one or more exhalations of air being passively sampled.

(102) A device for measuring a person's ventilation or metabolism metrics, the device comprising: a conduit shaped to receive one or more exhalations of air therethrough; and at least one gas sensor within a gas sampling chamber in fluid communication with the conduit and configured to passively sample the one or more exhalations of air by means of a positive or negative pressure differential together with pump assistance.

(103) A device according to clause 102, or any preceding or subsequent clause, wherein the device is configured to selectively change from a breath-mixing mode to a breath-by-breath mode by increasing the ratio of the pump flow rate to the flow rate of through the conduit.

(104) A device according to any one of clauses 99 to 103, or any preceding or subsequent clause, wherein the device is configured to reduce the power otherwise needed by the pump to maintain the flow rate through a sample line in the breath-mixing mode by at least 25 to 50%.

(105) A device according to any one of clauses 99 to 104, or any preceding or subsequent clause, wherein the device is configured to reduce the power otherwise needed by the pump to maintain the flow rate through the sample line in the breath-mixing mode by 50% or more.

(106) A device according to any one of clauses 99 to 105, or any preceding or subsequent clause, wherein the device is configured to reduce the power otherwise needed by the pump to maintain the flow rate through the sample line in the breath-by-breath mode by 10% or more.

(107) A device according to any one of clauses 98 to 106, or any preceding or subsequent clause, wherein a plurality of samples of said one or more exhalations of air are mixed together within the gas sampling chamber in the breath-mixing mode and wherein the gas sampling chamber is fully purged between respective said exhalations of air so as to enable measurement oximetry waveforms and/or capnography waveforms in the breath-by-breath mode.

(108) Apparatus including any new and inventive feature, combination of features, or sub-combination of features as described herein.

(109) Methods including any new and inventive steps, acts, combination of steps and/or acts or sub-combination of steps and/or acts as described herein.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. A device for measuring a person's ventilation or metabolism metrics, the device comprising:
   a conduit shaped to receive an exhalation of air therethrough;
   at least one gas sensor passively sampling said exhalation of air via a positive or negative pressure differential; and
   a pump which assists in said passive sampling, wherein the pump adjusts flow rates of sample portions of the exhalation of air passing through to the at least one gas sensor, until a slope formed by said flow rates of the sample portions versus flow rates of primary portions of the exhalation of air passing through the conduit, is constant;
   wherein the device operates in either breath-mixing and breath-by-breath modes; and wherein the device changes between said modes as a function of operation of the pump.

2. The device according to claim 1, wherein the pump adjusts the flow rates of the sample portions of the exhalation of air passing through to the at least one gas sensor so as to achieve a linear and/or proportional relationship between said flow rates of the sample portions of the exhalation of air passing through to the at least one gas sensor and said flow rates of the primary portions of the exhalation of air passing through the conduit.

3. The device according to claim 1, wherein the pump adjusts the flow rates of the sample portions of the exhalation of air passing through to the at least one gas sensor, such that the slope formed by the flow rates of said sample portions versus the flow rates of the primary portions of said exhalation of air through the conduit, is minimised.

4. The device according to claim 1, wherein passive sampling via the pressure differential results in a passive base said flow rate of the sample portion of the exhalation of air passing through to the at least one gas sensor, with the pump supplementing the said base flow rate of said sampling and thereby operating with reduced power.

5. The device according to claim 1, wherein the device includes a sample line via which the sample portion of the exhalation of air passes through to the at least one gas sensor, and wherein the device includes a processor which receives flow rate data for the conduit and the sample line, wherein the processor determines the extent to which the flow rate of the sample portion of said exhalation of air passing through the sample line must be increased to achieve a linear and/or proportional relationship between the flow rates of the sample portion of the exhalation of air and said flow rates of the primary portions of the exhalation of air passing through the conduit, and wherein the processor adjusts the pump based on said determination.

6. The device according to claim 1, wherein the device is a portable, head-worn device which includes a processor that determines or quantifies one or more aspects of a person's ventilation or metabolic metrics, including one or more of: a volume of consumed oxygen (VO2) and/or a volume of expired carbon dioxide (VCO2) based on ventilation and the gas concentration of said exhalation of air which are time aligned; minute ventilation; respiratory frequency (Rf); tidal volume (Tv); a fraction of expired oxygen (FeO2); a fraction of inspired oxygen (FiO2); fraction of inspired carbon dioxide (FiCO2); and/or fraction of expired carbon dioxide (FeCO2).

7. The device according to claim 1, including a restriction within the conduit, the restriction promoting flow of the sample portion of the exhalation of air through a sample line to the at least one gas sensor, the restriction being one or more of: a constriction, with the conduit being a venturi tube; an intermediate portion of the conduit having a cross-sectional area less than at least one of first and second end portions of the conduit; an orifice plate with said sample line in fluid communication therewith; a pressure valve; and/or a member configured to promote said positive or negative pressure differential within the conduit.

8. The device according to claim 1, wherein the device operates in either of said breath-mixing and breath-by-breath modes using a single flow path.

9. The device according to claim 1, wherein the at least one gas sensor primarily receives said sample portions of the exhalation of air via the pressure differential caused by the shape of the conduit, with power requirements on the pump thus being inhibited.

10. The device according to claim 1, wherein the pump is upstream of the at least one gas sensor.

11. The device claim 1, wherein the pump is downstream of the at least one gas sensor.

12. The device according to claim 1, wherein the at least one gas sensor comprises an oxygen sensor which is adjacent to the conduit.

13. The device according to claim 1, including a gas sampling chamber in communication with the at least one gas sensor, wherein in the breath-mixing mode, a plurality of said sample portions of several said exhalations of air are mixed together within the gas sampling chamber, and wherein in the breath-by-breath mode, the gas sampling chamber is purged multiple times per breath.

14. A device for measuring a person's ventilation or metabolism metrics, the device comprising:
  a conduit shaped to receive an exhalation of air therethrough;
  at least one gas sensor passively sampling said exhalation of air via a positive or negative pressure differential;
  a pump which assists in said passive sampling, wherein the pump adjusts flow rates of sample portions of the exhalation of air passing through to the at least one gas sensor, until a slope formed by said flow rates of the sample portions versus flow rates of primary portions of the exhalation of air passing through the conduit, is constant; and
  a gas sampling chamber in communication with the at least one gas sensor and having a volume, wherein the pump adjusts the flow rate(s) of the sample portion of the exhalation of air passing through to the gas sampling chamber such that a volume of exhaled air passing into the gas sampling chamber per said exhalation of air is selectively less than, equal to or greater than the volume of the gas sampling chamber.

15. The device according to claim 14, wherein the pump adjusts the flow rates of the sample portions of the exhalation of air passing through to the at least one gas sensor, such that the slope formed by the flow rates of said sample portions versus the flow rates of the primary portions of said exhalation of air through the conduit, is equal to a target said slope.

16. The device according to claim 14, including a battery to power the at least one gas sensor and the pump, with the pump being configured to minimally adjust the flow rates of the sample portion of the exhalation of air so as promote maximum life of said battery.

17. A device for measuring a person's ventilation or metabolism metrics, the device comprising:
  a conduit shaped to receive an exhalation of air therethrough;
  at least one gas sensor passively sampling said exhalation of air via a positive or negative pressure differential;
  a pump which assists in said passive sampling, wherein the pump adjusts flow rates of sample portions of the exhalation of air passing through to the at least one gas sensor, until a slope formed by said flow rates of the sample portions versus flow rates of primary portions of the exhalation of air passing through the conduit, is constant; and a gas sampling chamber in communication with the at least one gas sensor, wherein a plurality of samples of said one or more exhalations of air are mixed together within the gas sampling chamber in a breath-mixing mode, wherein the gas sampling chamber is purged multiple times per breath so as to enable measurement of one or more of oximetry waveforms and capnography waveforms in a breath-by-breath mode, and wherein the device selectively changes from the breath-mixing mode to the breath-by-breath mode by increasing the ratio of the flow rate of the pump to the flow rate of said exhalation of air through the conduit.

18. The device according to claim 17, wherein the device operates in either of said breath-mixing and breath-by-breath modes using a single flow path.

19. A device for measuring a person's ventilation or metabolism metrics, the device comprising:
  a conduit shaped to receive an exhalation of air therethrough;
  at least one gas sensor passively sampling said exhalation of air via a positive or negative pressure differential;
  a pump which assists in said passive sampling, wherein the pump adjusts flow rates of sample portions of the exhalation of air passing through to the at least one gas sensor, until a slope formed by said flow rates of the sample portions versus flow rates of primary portions of the exhalation of air passing through the conduit, is constant; and
  a gas sampling chamber in communication with the at least one gas sensor, wherein the pump adjusts the flow rate(s) of the sample portion of the exhalation of air passing through to the gas sampling chamber such that: multiple said exhalations of air are mixed together within the gas sampling chamber; or the sample portion of an initial said exhalation of air is purged by the sample portion of a subsequent said exhalation of air.

20. A method of measuring a person's ventilation or metabolism metrics, the method comprising:
  providing a conduit shaped to receive an exhalation of air therethrough;
  passively sampling the exhalation of air via a positive or negative pressure differential so as to direct a sample portion of the exhalation of air to at least one gas sensor;
  assisting the passive sampling of the exhalation of air via a pump;
  adjusting flow rates of the sample portion of the exhalation of air via the pump so as to obtain a linear and/or proportional relationship between said flow rates of the sample portion of the exhalation of air and flow rates of a primary portion of the exhalation of air passing through the conduit; and
  selectively changing between a breath-mixing mode, in which a plurality of said sample portions of several said exhalations of air are mixed together within a gas sampling chamber, to a breath-by-breath mode, in which the gas sampling chamber is purged multiple times per breath, by increasing the ratio of one or more flow rates of the pump to one or more flow rates of said exhalations of air through the conduit.

* * * * *